(12) United States Patent
Carlson

(10) Patent No.: US 7,263,399 B2
(45) Date of Patent: Aug. 28, 2007

(54) APPARATUS AND METHODS FOR ANALYSIS OF CARDIAC DEVICE STORED EPISODES CONTAINING SENSED SIGNALS AND WAVEFORMS

(75) Inventor: Dan B. Carlson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 691 days.

(21) Appl. No.: 10/135,910

(22) Filed: Apr. 29, 2002

(65) Prior Publication Data

US 2003/0204146 A1 Oct. 30, 2003

(51) Int. Cl.
*A61B 5/04* (2006.01)
(52) U.S. Cl. .................................... 600/509
(58) Field of Classification Search ................ 600/509, 600/510
See application file for complete search history.

(56) References Cited

U.S. PATENT DOCUMENTS

| | | | |
|---|---|---|---|
| 4,742,458 A * | 5/1988 | Nathans et al. ............. | 382/207 |
| 5,271,411 A | 12/1993 | Ripley et al. | |
| 5,345,362 A | 9/1994 | Winkler | |
| 5,354,319 A | 10/1994 | Wyborny et al. | |
| 5,383,909 A | 1/1995 | Keimel | |
| 5,843,139 A | 12/1998 | Goedeke et al. | |
| 6,016,442 A * | 1/2000 | Hsu et al. ................... | 600/518 |
| 6,091,986 A | 7/2000 | Keimel | |
| 6,171,256 B1 | 1/2001 | Joo et al. | |
| 6,217,525 B1 | 4/2001 | Medema et al. | |

* cited by examiner

Primary Examiner—Mark Bockelman
(74) Attorney, Agent, or Firm—Daniel G. Chapik; Girma Wolde-Michael

(57) ABSTRACT

Apparatus and methods for analyzing implantable medical device (IMD) data and to distinguish specific morphologies for review. EGM waveforms of a cardiac cycle can be grouped according to waveform shape similarities, preferably accomplished using clustering algorithms. The EGM waveform can be divided into segments represented by a one dimensional vector for each segment, and nearest neighbor vector clustering used to group the waveforms according to morphological similarity. The waveforms can be further grouped at a second level into chronologically contiguous similar EGM waveforms. Interval data for a cardiac cycle may also be grouped according to interval similarity and chronology. The chronologically contiguous waveform and interval groupings may be further grouped. Large quantities of EGM data are automatically analyzed and annotated to focus the attention of a cardiologist on likely areas of concern, reducing the need to visually inspect endless streams of EGM waveforms.

12 Claims, 25 Drawing Sheets

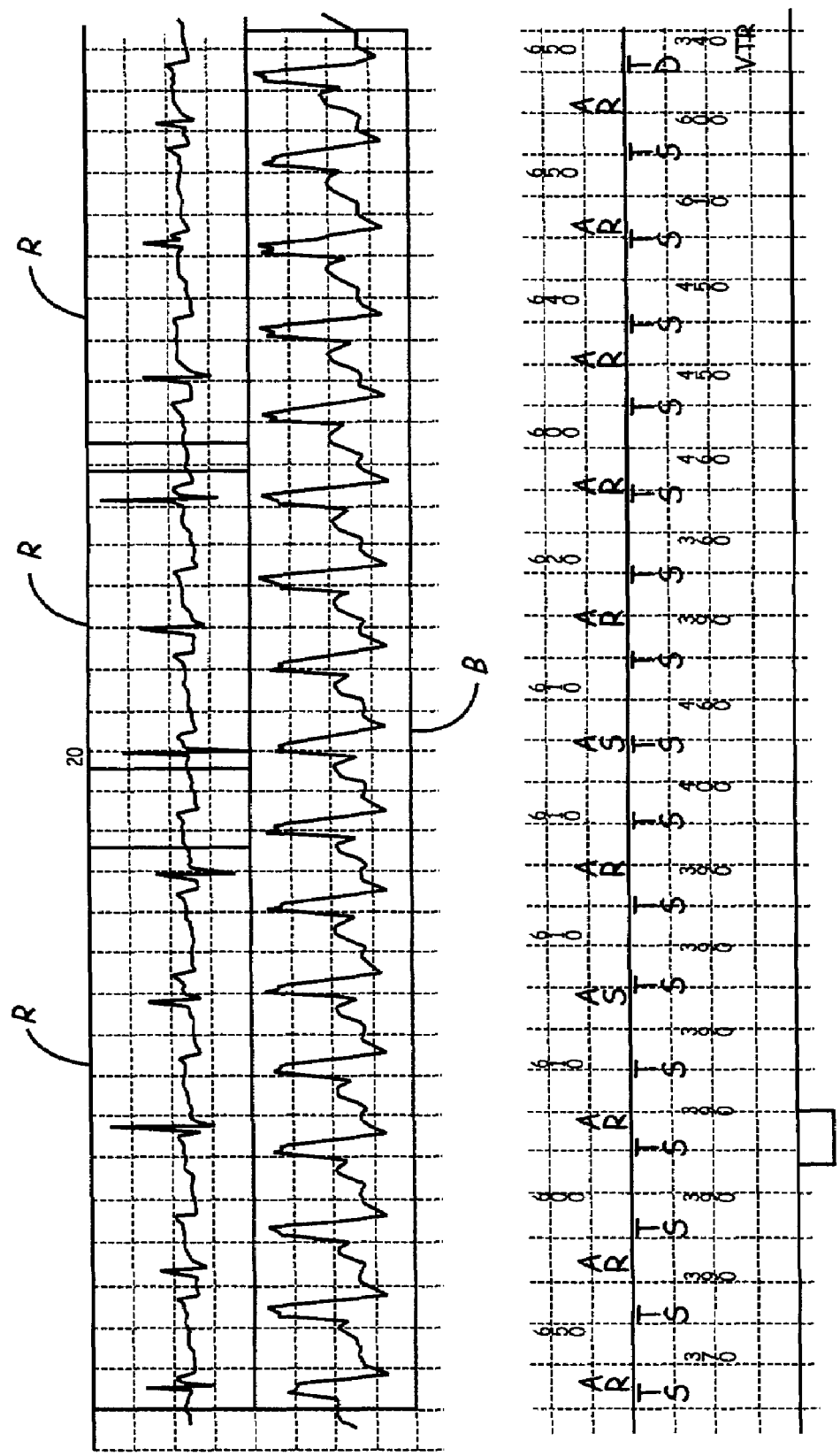

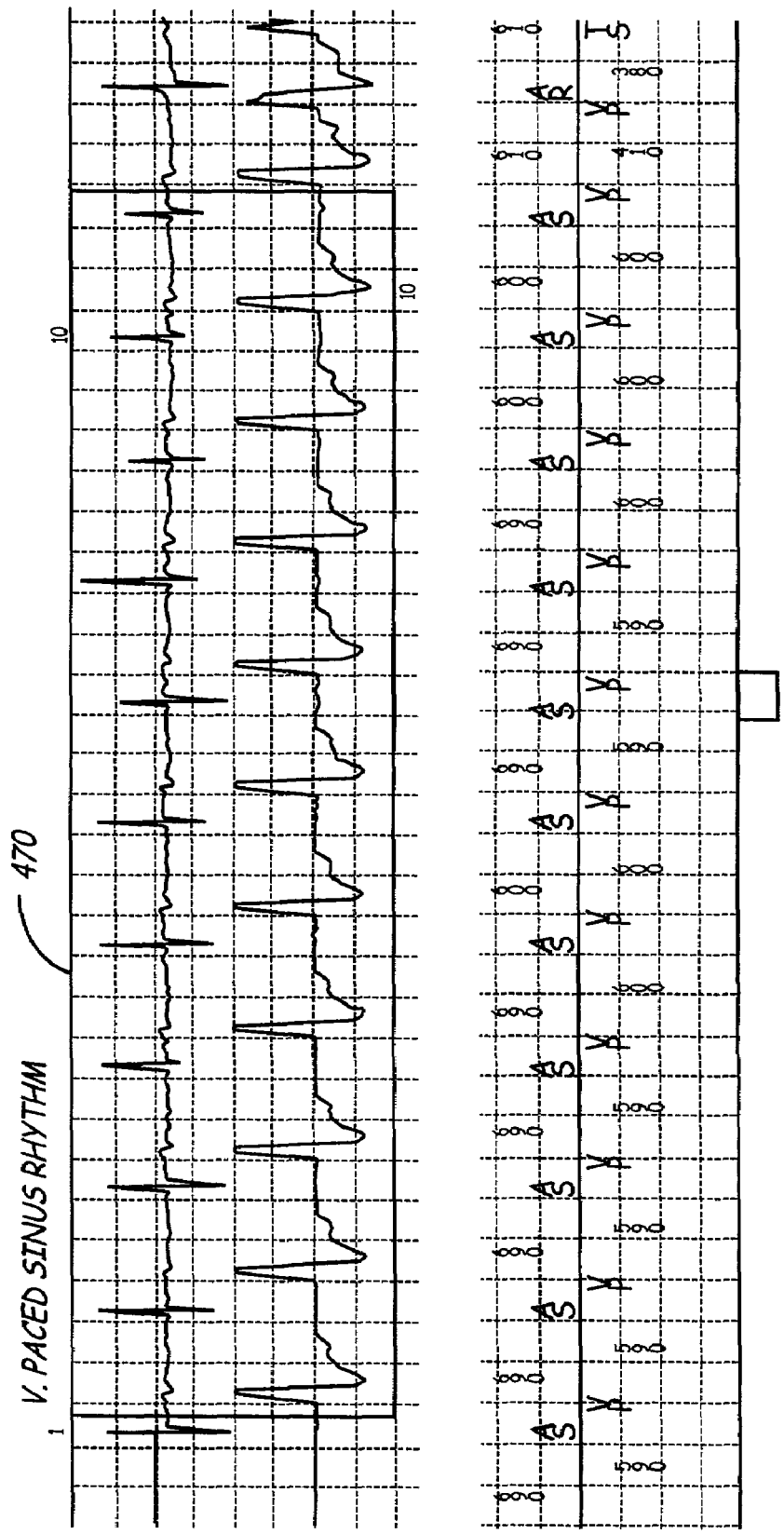

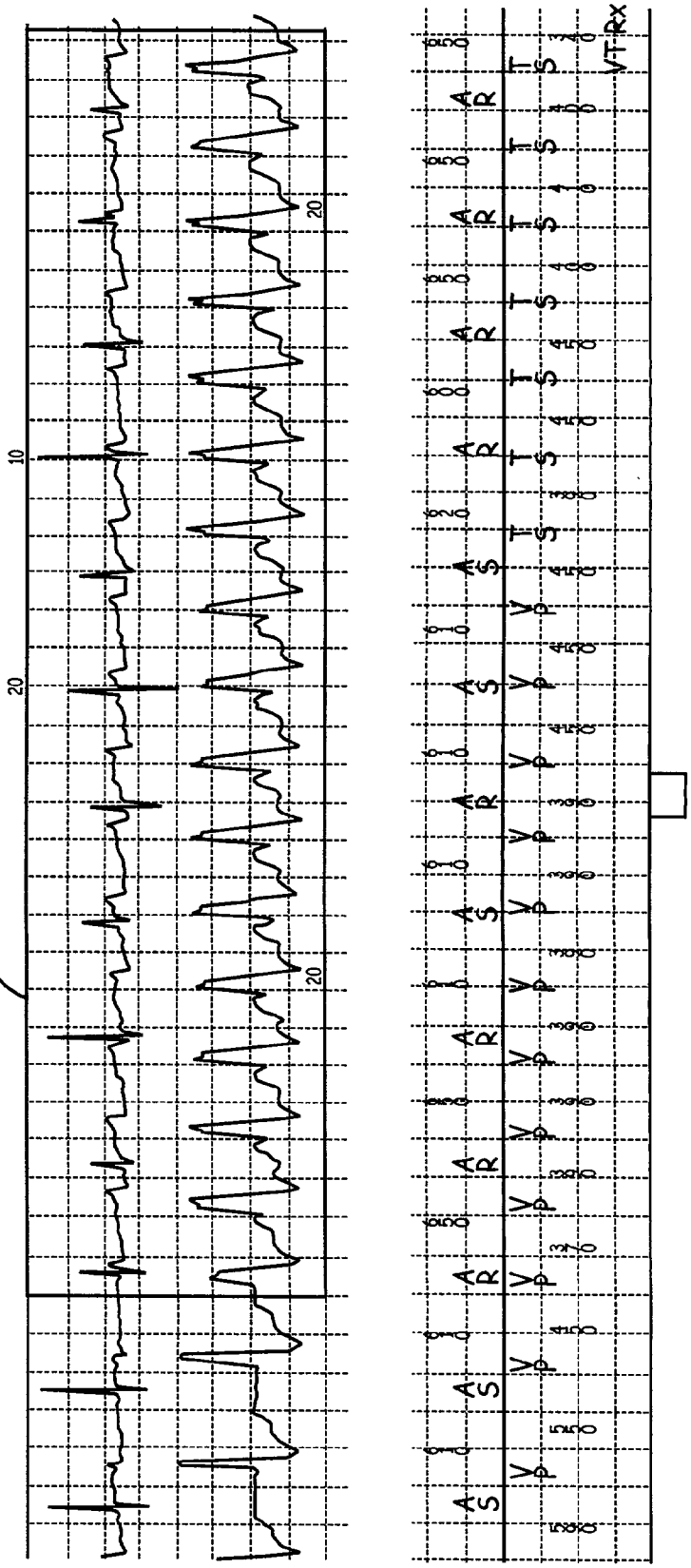

V. PACED SINNS

APPARATUS AND METHODS FOR ANALYSIS OF CARDIAC DEVICE STORED EPISODES CONTAINING SENSED SIGNALS AND WAVEFORMS

FIELD OF THE INVENTION

The present invention relates generally to cardiac devices. More specifically, the invention relates to apparatus and methods for analyzing and compiling, in a concise format, of cardiac episode such as sensor waveform data, EGM data, and implanted medical device (IMD) stored data including morphologies thereof.

BACKGROUND OF THE INVENTION

Advances in IMD and integrated circuit technology have made it possible to store large amounts of diagnostic and therapy data. In particular, IMDs including but not limited to cardiac pacemakers and implantable cardiac defibrillators, and cardioverters, increasingly have the capacity to store large amounts of data. The data may include EGM waveforms, interval data for various heart chambers, and marker data generated by the IMD processor based on analysis of the waveform data and their morphologies.

Stored data in IMDs is generally accessed via telemetry communications. Specifically, IMD data is downloaded by uplinking to a programmer using wireless telemetry. Examples of telemetry systems may be found in U.S. Pat. Nos. 5,354,319; 5,345,362; 5,383,909; 5,843,139; and 6,091,986, all herein incorporated by reference. The increased data storage capacity of IMDs requires navigation and review of various diagnostic and therapy episodes, thus creating difficulties in extracting data that may be of immediate use to physicians and healthcare providers. Specifically, physicians are being increasingly overwhelmed with the volumes of data they must interpret. The recent advent of in-home telemetry systems for retrieving and transmitting cardiac data over networks or the Internet will likely further increase the amount of data to be interpreted.

What would be desirable are apparatus and methods for alleviating the burden of data overload without sacrificing patient care. What would further be desirable are apparatus and methods for analyzing episodes stored IMDs so that concise clinical summaries of the data can be presented to the physician for quick analysis and review. Accordingly, apparatus and methods for immediately drawing the attention of the treating physician to cardiac patient data of likely concern would be most beneficial.

SUMMARY OF THE INVENTION

The present invention provides apparatus and methods for analyzing and processing data originating from devices that sense cardiac signals that vary over at least one cardiac cycle. The IMDs include sensors that sense electrical potential, magnetic field, pressure, impedance, fluid flow, fluid velocity, and cardiac muscle dynamics. Sensors include internal electrical potential sensors, for example, electrodes coupled to IMDs. Sensors also include external electrical potential sensors, for example, electrodes coupled to EKG machines and external defibrillators. The internal electrical sensors may be used to generate electrogram (EGM) waveforms while external sensors may be implemented to generate EKG waveforms. Other sensors can generate other cardiac waveforms, for example, pressure, magnetic field, motion, velocity, and impedance waveforms that vary periodically over the cardiac cycle. The invention can be used to analyze signals from a set of several sensors in the atrium and a set of several sensors in the ventricle.

Heterogeneous sensors, for example, electrical potential and pressure sensors both sensing the same heart chamber, can be used to sense heterogeneous waveforms that may be grouped together at various levels, for example, grouped into time blocks where there are repeating similar EGM waveforms and repeating similar pressure waveforms that share time blocks that substantially overlap in time, and may be deemed co-extensive. As disclosed herein, the present invention primarily implements internal electrical potential sensors to generate EGM waveform signals. The present application also uses interval data as an example of device generated data. These examples are non-limiting and depict only some of the uses of the present invention.

The present invention provides apparatus and methods for analyzing and processing data originating from IMDs. The apparatus and methods operate on EGM waveforms, interval data, and other distinguishing morphologies, grouping the data into multiple meaningful sets based both on beat similarities and chronology. The data can be retrieved as a data stream obtained directly from the implanted device in real-time, from data previously retrieved and stored in volatile or nonvolatile storage, or from a data stream stored in the IMD. In one embodiment, the data is retrieved over a data communications network, at a location remote to the IMD. The data from the IMD may include EGM waveform data, cardiac interval data, and IMD generated markers.

A further embodiment of the invention analyzes stored cardiac data in an IMD by retrieving the stored data relating to a first heart chamber and dividing the EGM waveform data into numerous EGM heartbeat waveform segments, where each EGM segment is associated with cardiac activity. The EGM waveform segments can be grouped into EGM waveform-similarity or identity-groups as a function of the waveform similarities based on their shape, also referred to as morphological similarities. The grouping is preferably performed by clustering the EGM waveforms according to the waveform shape or morphological characteristics. This grouping process can be viewed as a first level of EGM waveform grouping. In one embodiment, the grouping step includes calculating a waveform shape distance between the numerous EGM cardiac waveform segments and clustering the waveform segments as a function of the distance between the EGM cardiac waveform segments. In one exemplary embodiment, each EGM cardiac waveform segment is represented as a vector, a one-dimensional array, and the distance between two discrete waveforms is designated to be the distance between the two vectors. The vector distance is a Euclidean distance in some embodiments, or a Mahalanobis distance generally.

In a preferred embodiment, the clustering process utilizes nearest neighbor vector clustering. The first level of EGM waveform identity groups thus formed can be marked, stored, displayed, printed, output, and any combination thereof, depending on the method. In one embodiment, the EGM waveform segments are visually displayed together with a visual indicia of the EGM waveform identity group membership, for example, by enclosing similar EGM waveforms in similarly color coded or texturally coded boxes.

The first level of EGM waveform identity groups can be further grouped by collecting temporally adjacent EGM waveform segments that are in the same group into chronologically contiguous and similar waveform groups. The chronologically contiguous grouping of similar EGM waveforms may be viewed as a second level of grouping. The chronologically contiguous waveforms may include only perfectly temporally adjacent similar waveforms in some embodiments, while other embodiments allow for a one or two cardiac cycle distance between the similar waveforms. The second level grouping may be marked, stored, displayed, and output. In one embodiment, the chronologically contiguous and similar waveforms are displayed with a visual indicia of second level group membership, for example, by a color coded or texturally annotated box drawn over several of the EGM waveforms along the time axis.

In some embodiments, the stored cardiac cycle interval data is also analyzed. The interval data may be, for example, A to A or V to V intervals. In one embodiment, the implanted device interval data is retrieved for a first heart chamber and grouped into heart chamber interval identity groups, which may be viewed as a first grouping level for the interval data. The grouping step may include calculating the difference or distance between pairs of cardiac cycle intervals and clustering the intervals as a function of the distance between the intervals. In one method, nearest neighbor clustering is used to group the intervals.

Sufficiently similar intervals can be further grouped by collecting temporally adjacent intervals having the same interval identity group membership into chronologically contiguous similar interval identity groups, which may be viewed as a second level grouping of the intervals. The chronologically contiguous group membership may require perfect adjacency, or allow for a one or two cardiac cycle distance. The intervals may be marked, stored, and/or displayed, as previously discussed with respect to the EGM waveforms. In one method, the intervals are color coded or texturally annotated to indicate interval identity group membership, and be enclosed by boxes to indicate the second level of chronologically contiguous interval group membership.

With the EGM waveforms and intervals being grouped by identity at a first level and grouped by chronology at a second level, the data can be further analyzed. The beat data can also be grouped into chronologically co-extensive, co-terminus, or co-pending beat regions having both substantially the same chronologically contiguous and similar EGM waveforms and chronologically contiguous and similar intervals. The results of the third level of grouping may be visually indicated by enclosing the appropriate group members in a box drawn about both the member EGM waveforms and intervals for a heart chamber.

The data for a second heart chamber may also be retrieved and processed as described above with respect to the first heart chamber. The EGM waveforms and beat interval data may be grouped into first level identity groups and second level chronological groups. The second chamber data may be further grouped into the third level of chronologically co-extensive groups described with respect to the first heart chamber.

The third level of chronologically co-extensive groups for the first heart chamber and the second heart chamber may be further grouped into fourth level groups each having chronologically co-extensive first and second heart chambers segments each having substantially the same third level group memberships. The fourth level groups each may be visually indicated by drawing a color coded or texturally annotated box to encompass both the first and second chamber EGM waveforms where appropriate. In one embodiment, the box would encompass the EGM waveforms for both the atrium (A) and the ventricle (V). The fourth level of chronologically co-extensive first and second chamber groupings may be further analyzed and classified using classification techniques. The EGM waveforms and beat interval data may be statistically processed and output for each fourth level grouping, for physician review. Methods in accordance with the present invention may also indicate that no patterns or groupings worthy of notation and interest were found over a certain time segment. In particular, the lack of chronologically contiguous or contemporaneous groups that satisfy higher level grouping requirements may be noted in the program output.

The present invention enables analysis and compilation of large quantities of IMD data. Specifically, cardiac data is meaningfully grouped and displayed based on EGM waveforms and cardiac cycle intervals. In particular, EGM morphologies and intervals may be grouped, respectively, or EGM morphologies and intervals can be grouped together. Further, A and V intervals can be grouped together. The groupings can provide visual indications of regions likely to be of little interest to a physician together with regions likely to be of concern. The attention of a cardiologist may thus be focused immediately upon an EGM region of interest, reducing the need to visually examine endless streams of EGM waveform and IMDs.

In another aspect, the invention provides apparatus and methods for compressing long regions of similar patterns and also for selecting an example of a repeating similar waveform, an "exemplar waveform", for visual display and/or presentation to a physician. A long repeating block or group of repeating similar waveforms, indicating either normal rhythm or arrhythmia, are visually compressed in one embodiment, by displaying the waveforms at either end of the block together with an omitted break region in between indicating the time/or number of cycles of the break and/or the entire compressed time block. In another embodiment, a waveform exemplar is displayed together with the time length and/or number of repetitions. Exemplar waveforms can be selected from the end time regions, middle, selected to have an average morphology within the group, or even selected randomly from the group of waveforms previously grouped according to similar waveform grouping criteria.

DETAILED DESCRIPTION OF THE PREFERRED EMBODIMENTS

Figure 1:
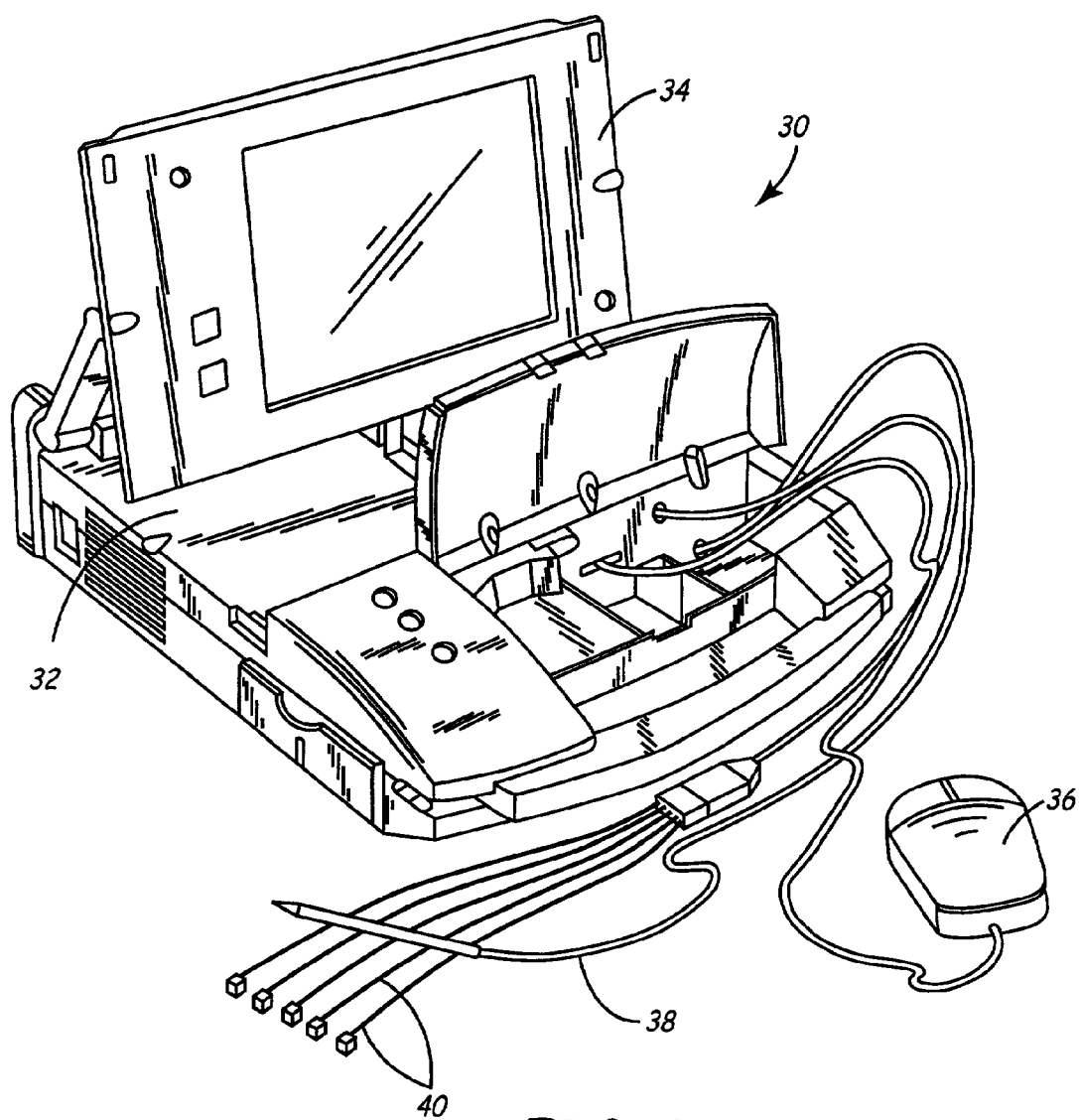
FIG. 1 is a perspective view of a computer device capable of receiving implanted cardiac device data through a telemetry peripheral, and capable of executing programs incorporating methods of the present invention.

FIG. 1 illustrates a computer device 30 for directly receiving implanted device data from an implanted pacemaker or implanted cardioverter defibrillator. Device 30 includes generally an external case 32, a display 34, a telemetry peripheral or programming head 36, a stylus 38, and numerous ECG leads 40. In one such device, the display is a touch screen, which can be used in conjunction with stylus 38 to select and input data. A device such as device 30 can serve multiple purposes, including programming implanted cardiac devices, reading ECGs, and retrieving data including EGMs, interval data, and marker data. Methods according to the present invention may be executed as a computer program on any general purpose computer, with the data being received through conventional data stores or streams, and the results displayed and stored on conventional computer displays and data storage devices, respectively.

Figure 2A:
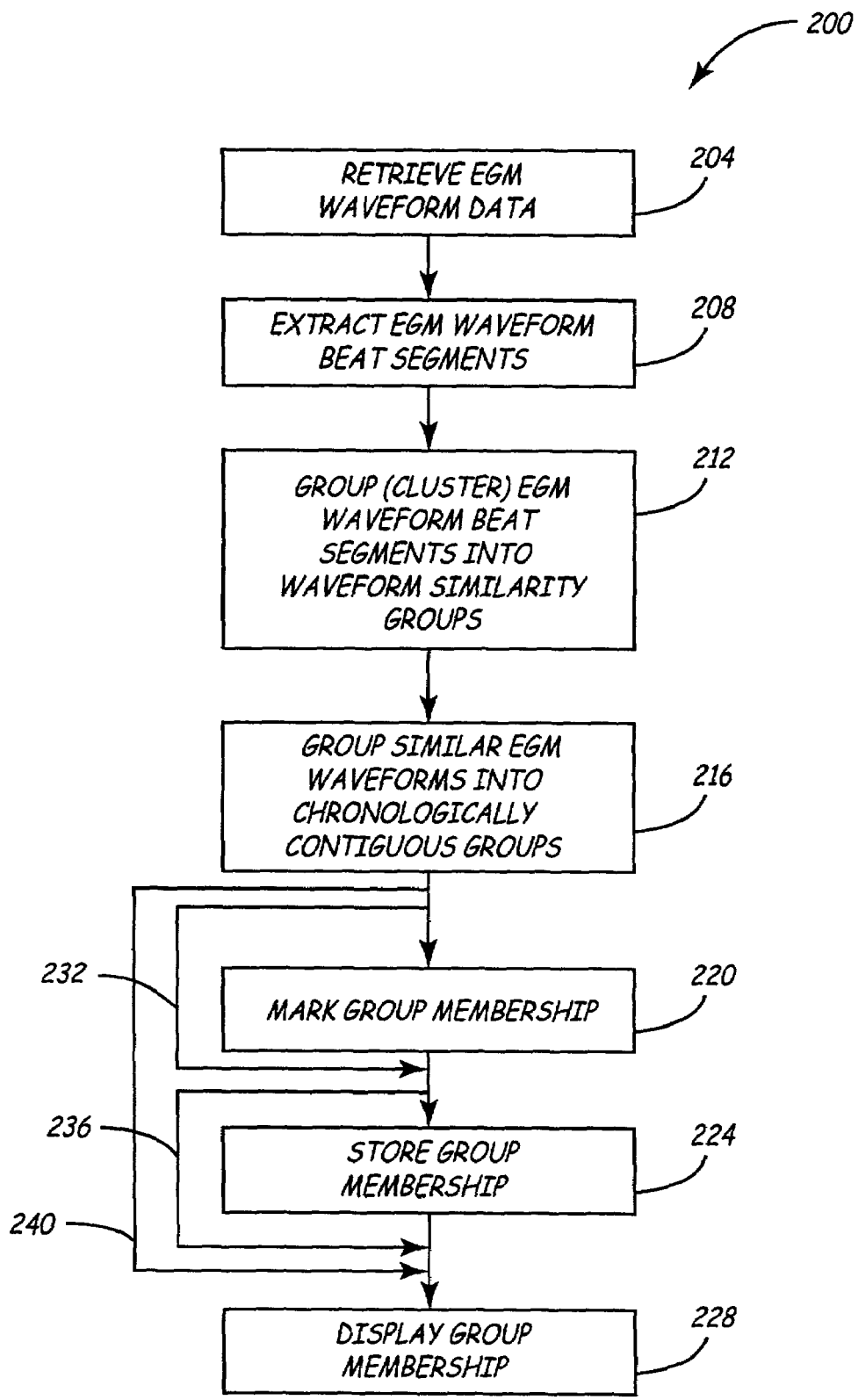
FIG. 2A is a flow chart of a method for grouping EGM waveforms into waveform similarity groups and further grouping the similar waveforms into chronologically contiguous similar waveform groups.

FIG. 2A illustrates a logic step for a computer-implemented process or method 200 which can be used to process or analyze EGM waveform data collected from an IMD. The IMD can be, for example, a pacemaker, or a cardioverter defibrillator. The EGM data can include waveform data including EGM waveform millivolt values at numerous time intervals. The EGM waveform data may be regularly distributed over time over numerous heartbeats or may be preferentially distributed near the heartbeat P or R waves. In one method, the EGM waveform data is represented as a series of integers represented scaled millivolt values, with time represented either inherently by position in a record or including explicit time stamp data together with the amplitude data. In one embodiment, the EGM waveform data is a very long stream or array of amplitude data for numerous cardiac cycles, where the cardiac cycles are considered centered about the P or R waves, depending on the chamber.

Method 200, and other methods of the present invention, can be computer-implemented as a program capable of being executed in a general purpose or a special purpose computer. Method 200, and other methods of the present invention, may be executed in either the same device used for retrieving EGM data from an implanted device or in a general purpose computer operating on data initially retrieved by another device having peripherals adapted to directly retrieve the EGM data from the implanted device. Method 200, and other methods of the present invention, may also be embodied in a computer program stored in computer readable media adapted to be read and executed by a general purpose computer. Method 200 and the other methods described in the present application may be stored as executable computer programs in non-volatile computer readable media including removable flash memory, computer diskettes, computer disks, CD ROMs, DVDs, and the like. While more than one chamber's data can be processed using method 200, the method is best understood as operating on a single chamber data at a time.

The program is initiated by EGM waveform data at step 204. The EGM waveform data may be retrieved directly from the IMD, from a data stream originating from the IMD or from a previous set of stored EGM waveform data. In one embodiment, the retrieved EGM waveform data is stored as a very long array or stream of EGM amplitude data. The EGM data retrieved is typically for an episode, containing the waveforms of numerous heartbeats. An episode can be any set of beat data, but is often a chronologically contiguous set of beats, and most often a set of chronologically contiguous beats including an arrhythmia, quite often requiring corrective action by the pacemaker or cardioverter defibrillator. Some episodes can contain between 10 to 100 beats.

Step 208 includes extracting EGM waveform beat segments from areas of interest disposed about each beat. The extracting step can be used to divide up the very long EGM waveform data into beat segments, with each beat segment including EGM waveform data for that beat. In some methods, the extracting step simply divides up the long EGM waveform data in to more manageable segments without discarding any data. In a preferred method, the extracting step selectively extracts EGM waveform data located near the P or R wave. The data located near the P or R wave is of more interest than the primarily iso-potential data located midway between the peak complexes of adjacent heartbeats. In some methods, the extracting step aligns the beat segments on a peak by extracting data located at a specific time or number of elements to either side of a prominent waveform feature, such as the P or R wave peak, to aid in comparing the waveforms at a later time. In other methods, the markers from the implanted device are used to identify the peak position and used to align the data in the segments. In a preferred embodiment, the extracted EGM waveform data in the segments is stored as an array or vector, with each EGM waveform data element occupying one element of the vector, with successive EGM waveform data points occupying successive elements along one dimension of the vector.

Step 212 includes clustering the EGM waveform beat segments into morphological or waveform identity groups, with each group having a morphological or shape identity between the members of that group. Clustering step 212 clusters the EGM waveform beat segments according to morphological identity, without having previous knowledge of the groups into which the waveform segments will be grouped. As used herein, the term "clustering" refers to a procedure that attempts to identify and extract similar groups from a data set. Unlike classification procedures, the number and memberships in the groups are not known a priori. In some methods, the clustering process is agglomerative, where each record starts as its own cluster and is merged with other clusters. In a preferred embodiment, the clustering is divisive, where all the data start in a single large cluster and is gradually broken down into smaller, more homogeneous clusters. Clustering is discussed in more detail below.

In some methods, the morphological identity groups are immediately displayed with some indicia of group membership, stored, and/or output to a data stream. The morphological identity group members of step 212 may or may not be chronologically successive or adjacent to each other. The members of a identity group are typically both found together and dispersed over the episode. Beat segments having the same morphological identity group membership may be thus grouped together chronologically or be separated chronologically from other group members. In a preferred embodiment, the morphological similarity groups are further processed, but can also be output or displayed directly. Step 212 may be considered to group the EGM waveforms at a first level.

Step 216 organizes chronologically contiguous similar waveform segments into a second level of chronologically contiguous beats. Chronologically contiguous waveforms having the same morphological identity group membership as determined in 212 can be further grouped together chronologically. In some embodiments, the group need not have perfect chronological adjacency for the morphologically similar waveforms. In particular, in some embodiments, morphologically similar beats may be grouped even if morphologically dissimilar waveforms are interposed within the collection. In one example, morphologically similar waveforms are considered substantially contiguous if they are located no more than one cardiac cycle distance away from another morphologically similar waveform. In another example, a distance of two cardiac cycles is allowed while still considering the beats to be substantially contiguous. Step 216 may be considered to group the EGM waveforms at a second level.

In step 220, the waveform groups of step 216 can be marked with some indicia of group membership prior to storage. In one example, the groups are stored as data structures or objects having collection and group identity stored as an attribute of the data structure or object. Group membership marking in general can be stored as attributes set within a data structure or object, as pointers from or to a member of the group, and as inheritance, with objects derived from other objects, and the like. In step 224, the waveform groups may be stored to non-volatile storage and/or output to a data stream. The collections may be stored as data structures and/or as objects.

Step 228 displays the marked waveform groups visually for human inspection. In one embodiment, each beat is marked with an indicia of morphological identity group membership, for example, a textual marker. In a preferred embodiment, the waveform groups are visually indicated by a box or a rectangle drawn about all beats considered to be members of the same chronologically contiguous and similar waveform groups. In one embodiment, displaying step 228 includes visually drawing a box on a computer display around the EGM plot for the heart chamber generating the EGM data.

As indicated by flow control arrow 232, marking step 220 may be bypassed in some embodiments. Further, as indicated by flow control arrow 236, in some embodiments, storing step 224 may also be bypassed. Furthermore, as indicated by flow control arrow 240, in some embodiments, both marking step 220 and storing step 224 may be omitted, with flow of control proceeding directly to displaying step 228.

Figure 2B:
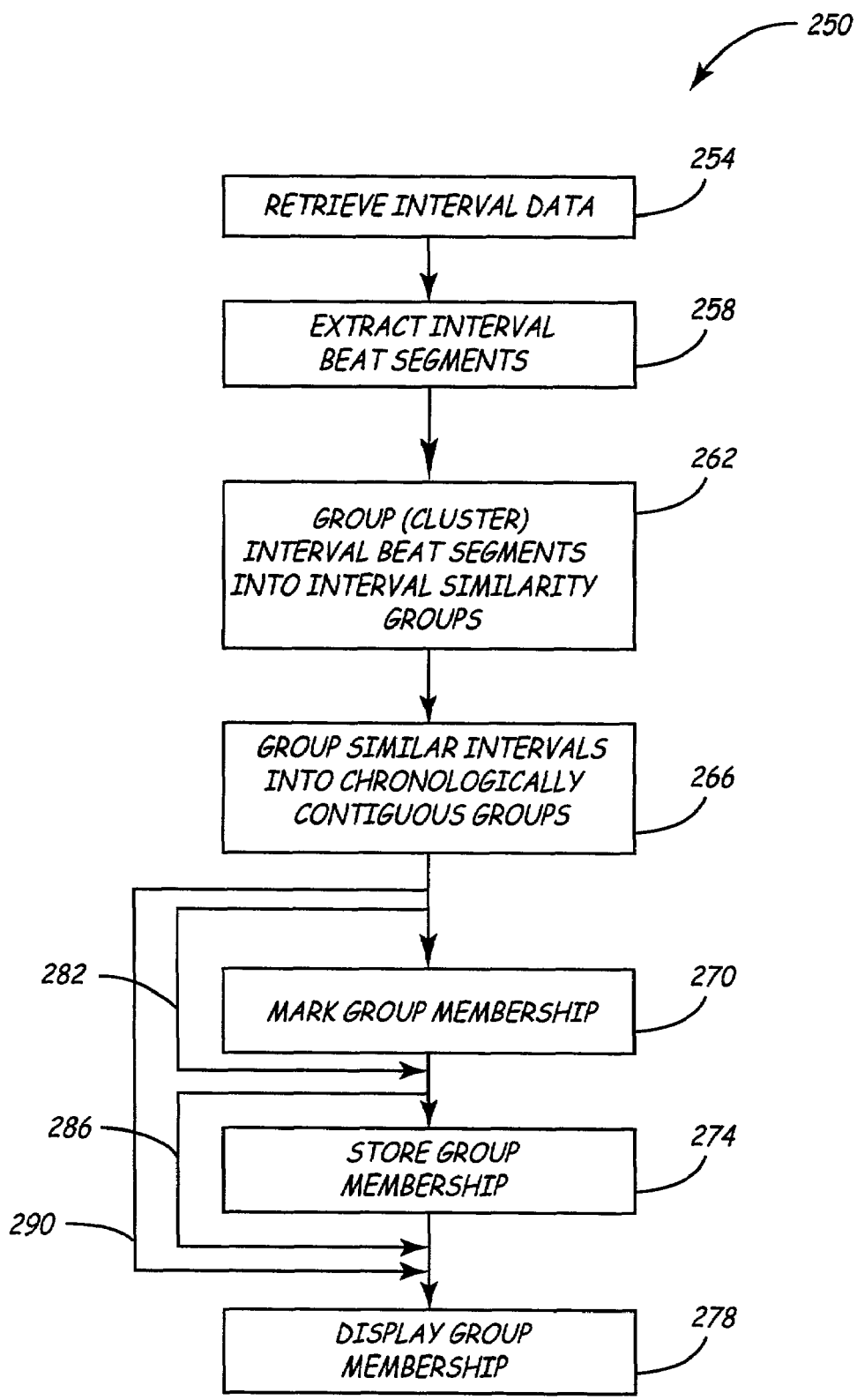
FIG. 2B is a flow chart of a method for retrieving implanted cardiac device interval data, grouping the interval data into similarity groups, and further grouping the interval data into chronologically contiguous similar interval groups.

FIG. 2B illustrates an embodiment 250 which may be used to preprocess or analyze interval data for a heart chamber. The interval data can be a time interval between significant atrial or ventricular events. The intervals can be, for example, an A-to-A interval, an A-to-V interval, or a V-to-V interval. In yet another embodiment, the interval information is newly deduced from the EGM waveform. In another embodiment, however, the interval information is retrieved from the IMD. In a preferred embodiment, the markers from the IMD are also retrieved, which include the marker annotations from the IMD indicating the identity of the events as interpreted by the IMD. Method 250 may be viewed as operating on interval data from a single heart chamber at a time.

In step 258, intervals are extracted for each cardiac cycle. In one example, for an atrium, a succession of A-to-A intervals are extracted. Each interval may thus have a single value, which can have units of milliseconds.

In step 262, the intervals extracted from step 258 are clustered into interval identity groups. Intervals that have values numerically close to each other may thus be grouped into interval identity groups, while the intervals having significantly different values may be separated into distinct groups. Two distinct interval identity groups may thus be viewed as two distinct clusters of numbers clustered about two points along a number line or axis.

In step 266, chronologically contiguous interval identity groups are organized into chronological groups. Step 266 can operate in a manner similar to step 216 discussed with respect to method 200. After the interval identity groups are organized into the collections in step 266, a marking step 270 may be executed to mark the collections in a meaningful way. In step 274, the collections may be stored to non-volatile storage and/or output to a data stream. In step 278, the collections of interval identity groups may be displayed on a display device. In one method, a box or a rectangle is drawn about the interval data on an EGM plot to encompass chronologically contiguous similar intervals. As previously discussed with respect to method 200, in some methods, beats may be considered chronologically contiguous or substantially contiguous if only separated from each other by one or a small number of beats. As indicated by flow control arrows 290, 282, and 286, marking step 270 and/or storing step 274 may be omitted.

Figure 2C:
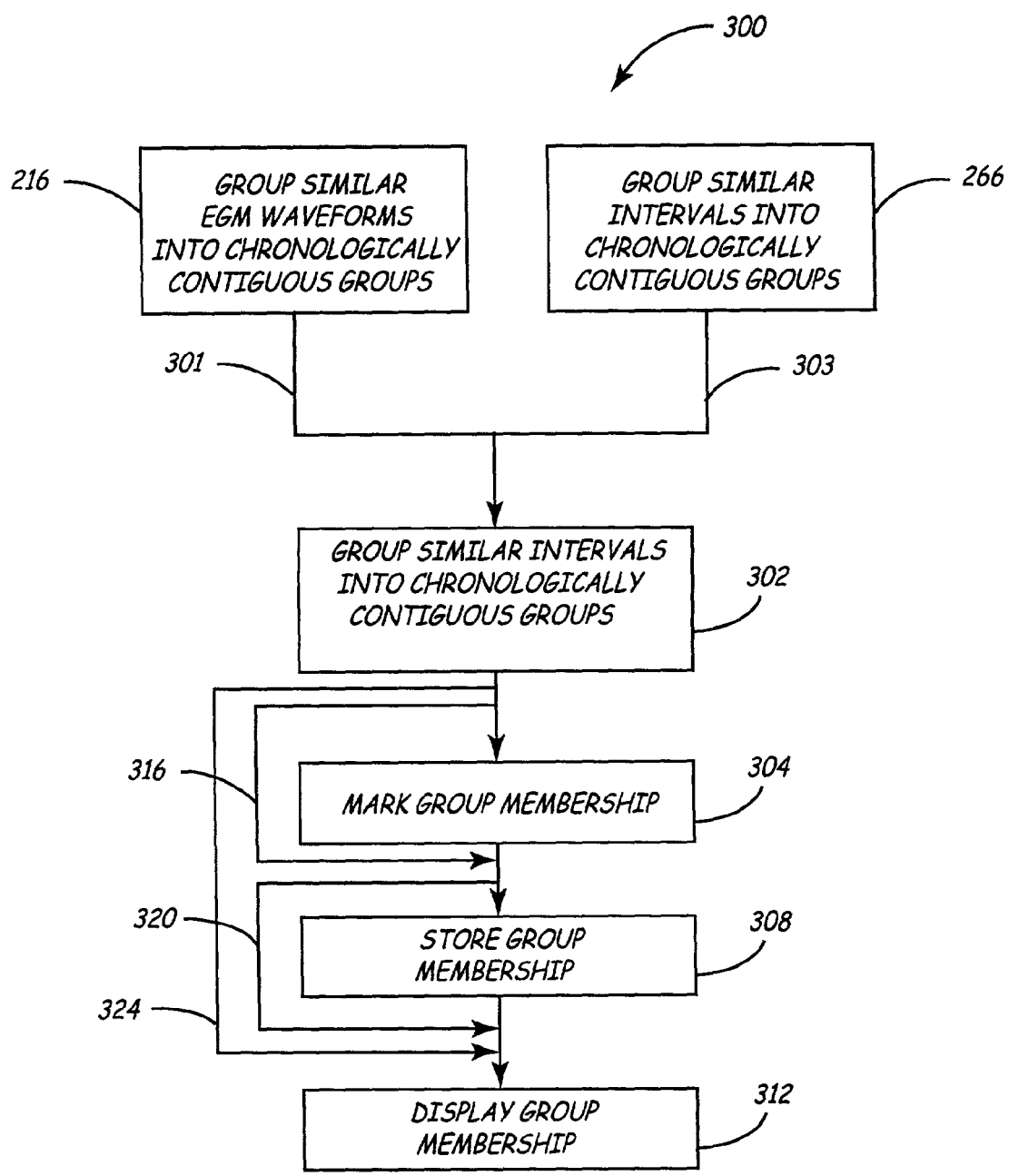
FIG. 2C is a flow chart of a method for accepting the outputs of FIGS. 2A and 2B and grouping the chronologically contiguous EGM waveform and interval data into chronologically co-extensive groups for a single heart chamber.

FIG. 2C illustrates an embodiment 300 which may be used to further group the EGM and interval data into a meaningful collection for later analysis or display. In embodiment 300, the chronologically contiguous morphologically similar waveform collections output from step 216 of method 200 may be obtained as indicated at step 301. Similarly, the chronologically contiguous similar intervals from step 266 of method 250 may be retrieved as indicated at step 303.

Step 302 locates or defines chronologically contemporaneous or coextensive collections of similar EGM waveforms and similar intervals. Step 302 may be understood by visualizing a first rectangle or rectangles drawn around EGM waveform plots and a second set of rectangles drawn about the EGM interval data. Where the amplitude and interval collection boxes are chronologically coextensive or substantially coextensive, a third larger rectangle may be visualized as encompassing both the EGM waveforms and the intervals. The combined EGM waveform groups and the interval groups defined by step 302 may be considered to be third level groups.

In step 304, the groups of step 302 can be marked with some indicia of group membership. In step 308, the groups may be stored in non-volatile storage and/or output to a data stream. In step 312, the groups may be displayed on a computer display device. In one embodiment, the groups are displayed as lines or boxes drawn about both the appropriate EGM waveform groups and the interval groups for one chamber. As indicated by flow control arrows 324, 316 and 320, marking step 304 and/or storing step 308 may be omitted in some methods.

Figure 2D:
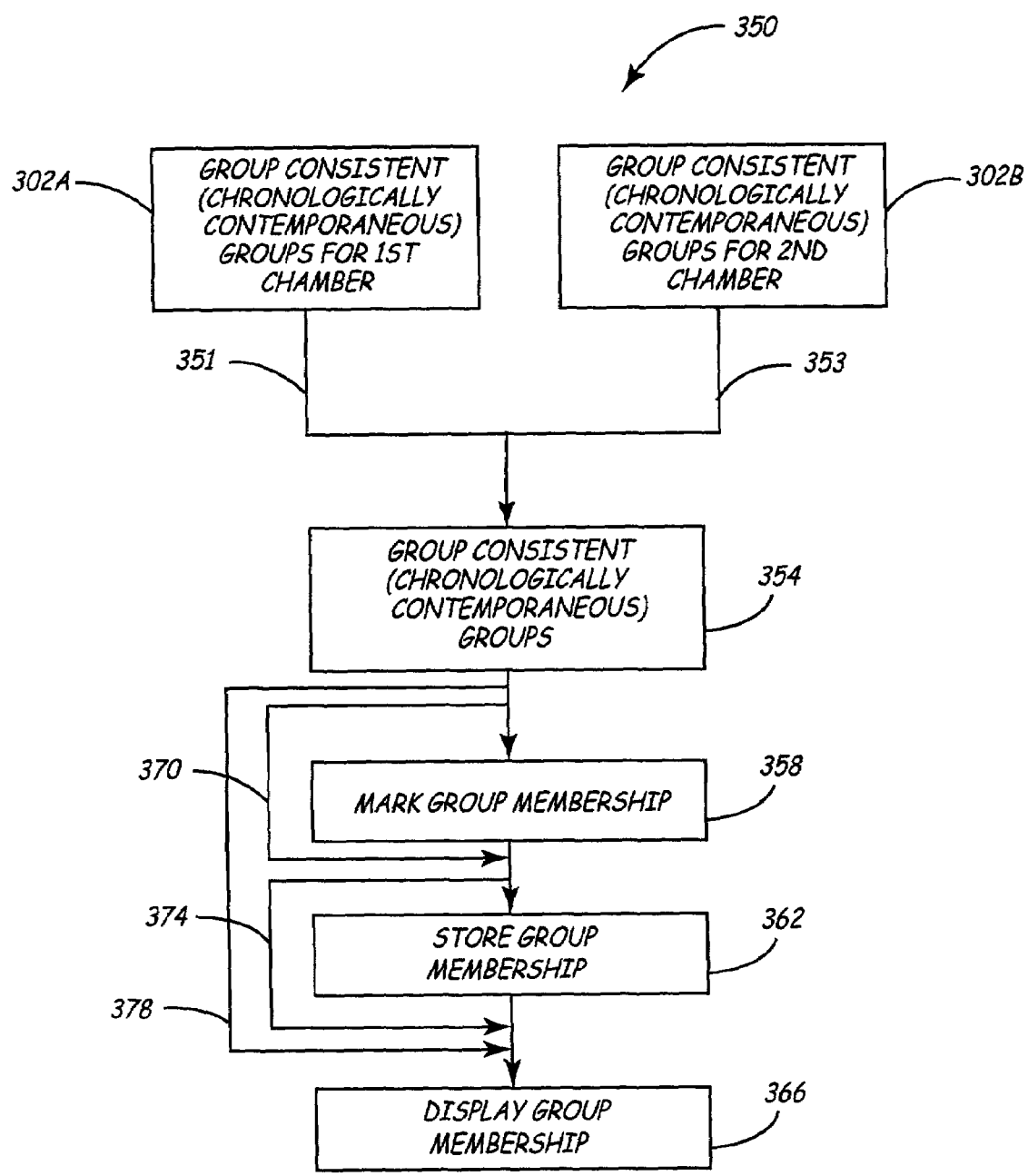
FIG. 2D is a flow chart of a method for accepting the output of FIG. 2C for two heart chambers and grouping the similar and chronologically co-extensive portions into a group including the appropriate EGM and interval data for both chambers.

FIG. 2D illustrates embodiment 350 which may be used to further group the EGM data for analysis or immediate visualization. Method 350 may be used to group EGM and interval data from two heart chambers to further aid in processing or analysis. In step 302A, the groups including both EGM and intervals for a first heart chamber are obtained, as discussed with respect to step 302 in FIG. 2C. Similarly, in step 302B, a group of appropriate EGM waveforms and interval are obtained as described with respect to step 302 of method 300 in FIG. 2C. As indicated by flow control line 351 and 353, the groups are fed to step 354.

In step 354, chronologically contemporaneous or co-extensive groups from steps 302A and 302B may be found and used to form a fourth level grouping of EGM and interval data. The fourth level collection may thus include EGM waveforms and intervals for a first chamber as well as similar EGM waveform and intervals data for a second chamber. In one embodiment, the fourth level grouping includes morphologically similar EGM waveforms for the atrium, similar intervals for the atrium, morphologically similar EGM waveforms for the ventricle, and similar intervals for the ventricle. The operation of step 354 may be visualized by drawing a rectangle or circle about the previous groupings of atrial and ventricular EGM waveform and interval similarities previously discussed.

The groups output from step 345 may be marked with some indicia of group membership in step 358. The fourth level groupings may be stored in step 362, and displayed in step 366. As indicated by flow control arrows 378, 370, and 374, the marking and/or storing steps 358 and 362 may be omitted in some methods.

Figure 3:
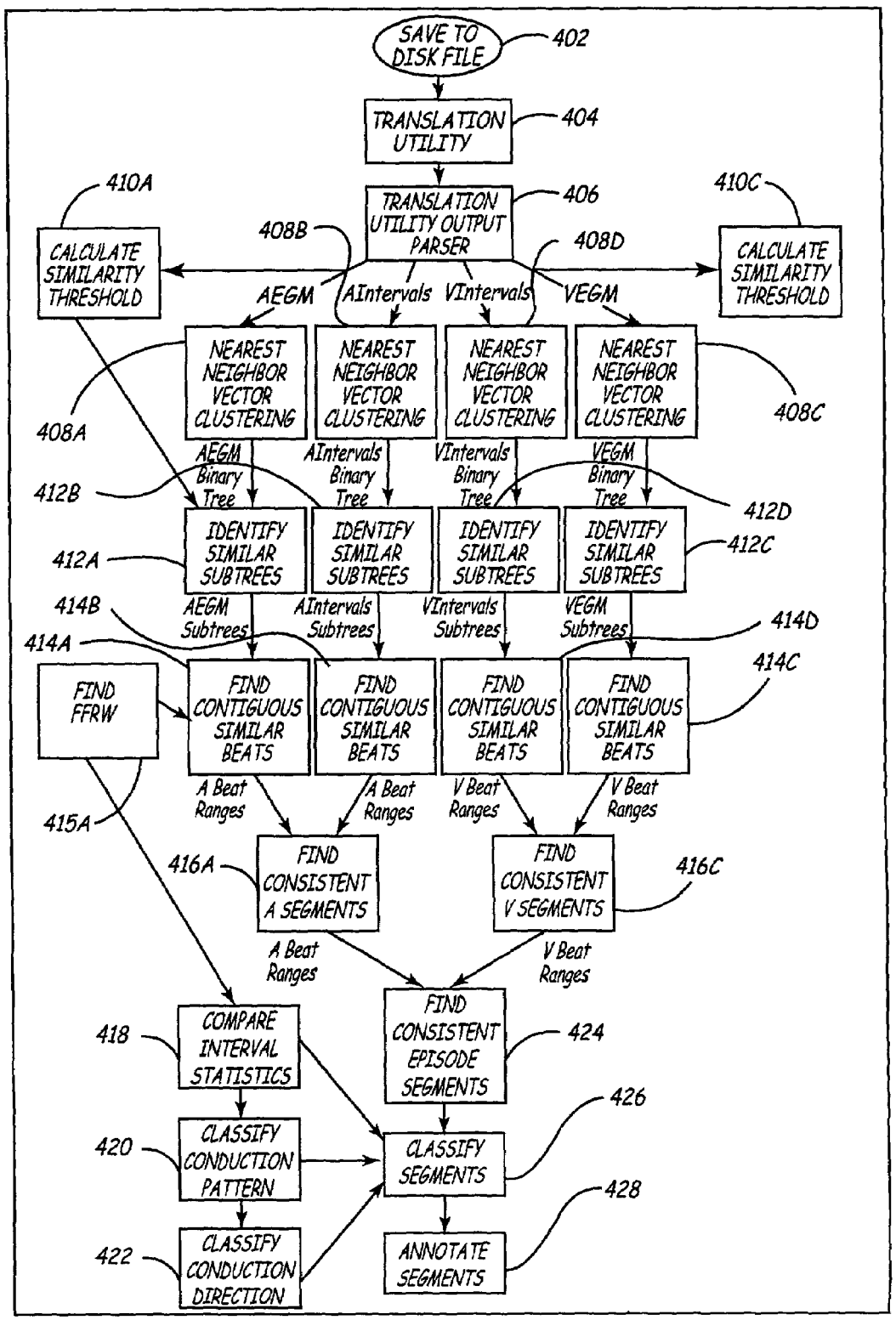
FIG. 3 is a flow chart of a method for retrieving EGM waveform data and implanted device data, grouping the data at increasingly higher levels, and outputting the results.
Figure 4A:
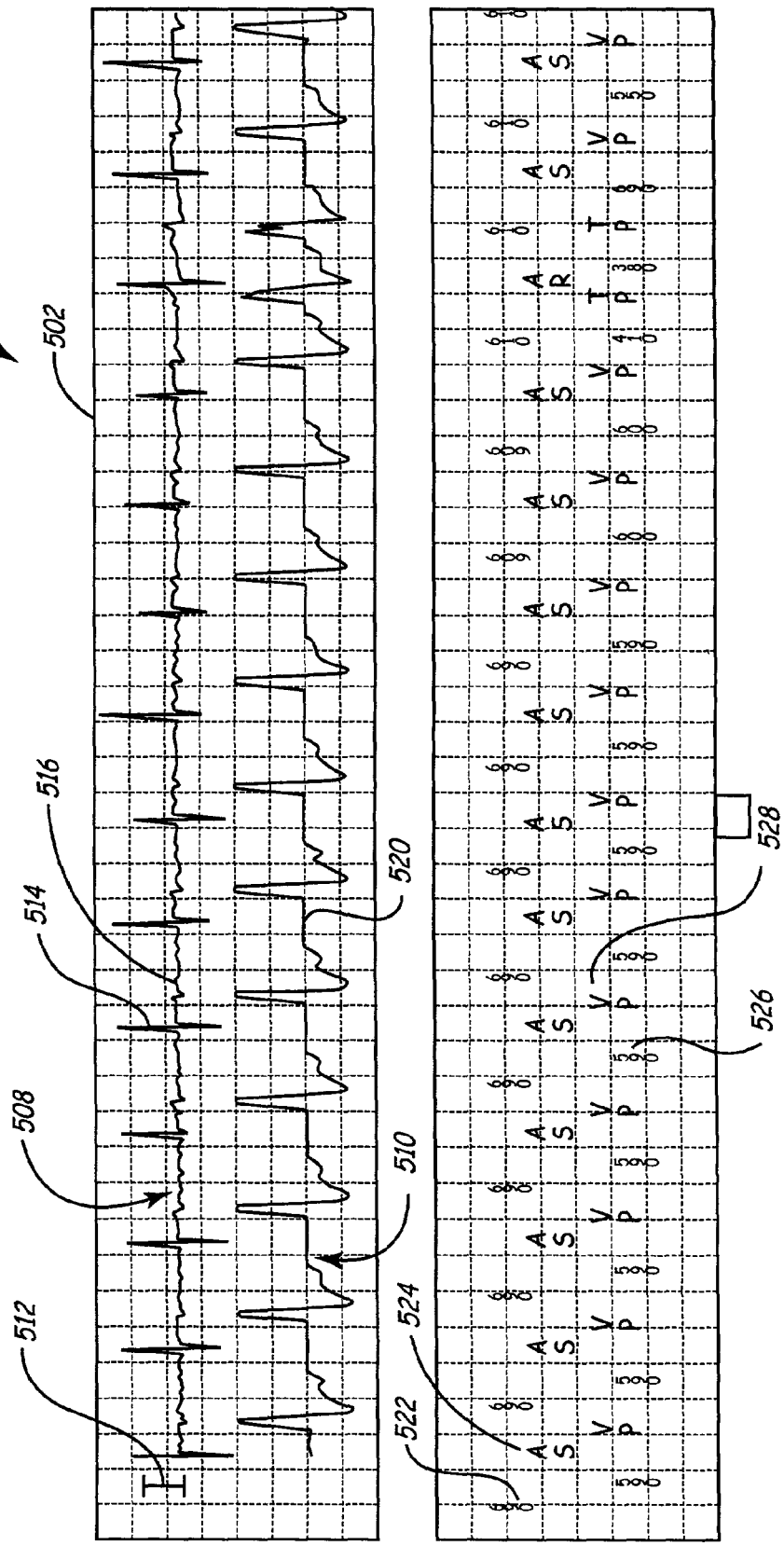
FIG. 4 is a strip chart output of atrial and ventricular EGM, interval, and marker data, for a single episode.
Figure 4B:
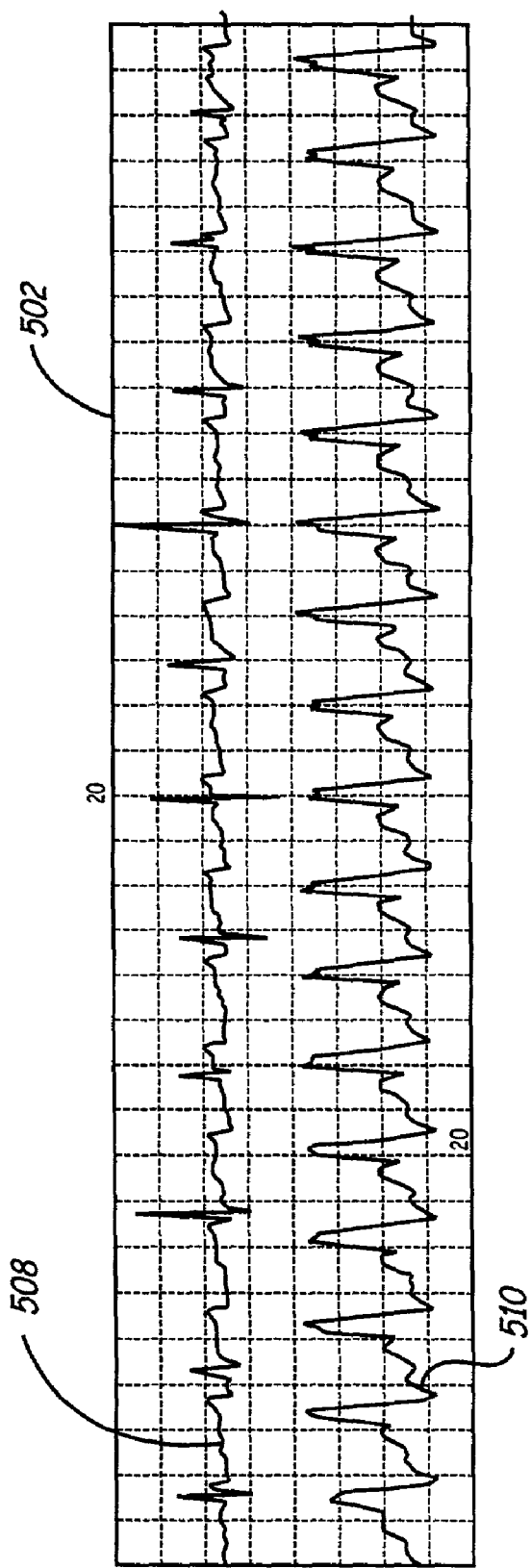
Figure 4B:
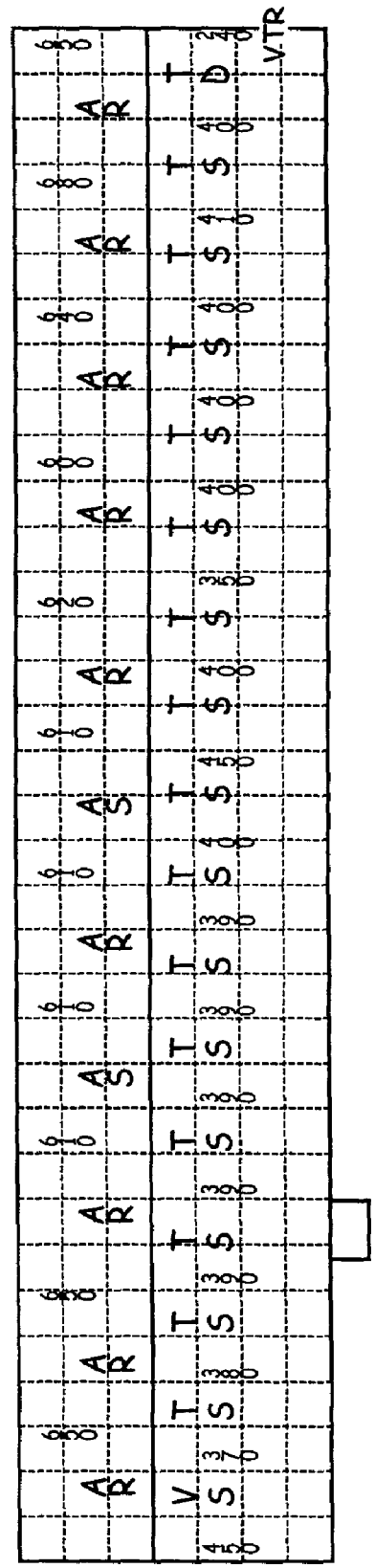
Figure 4C:
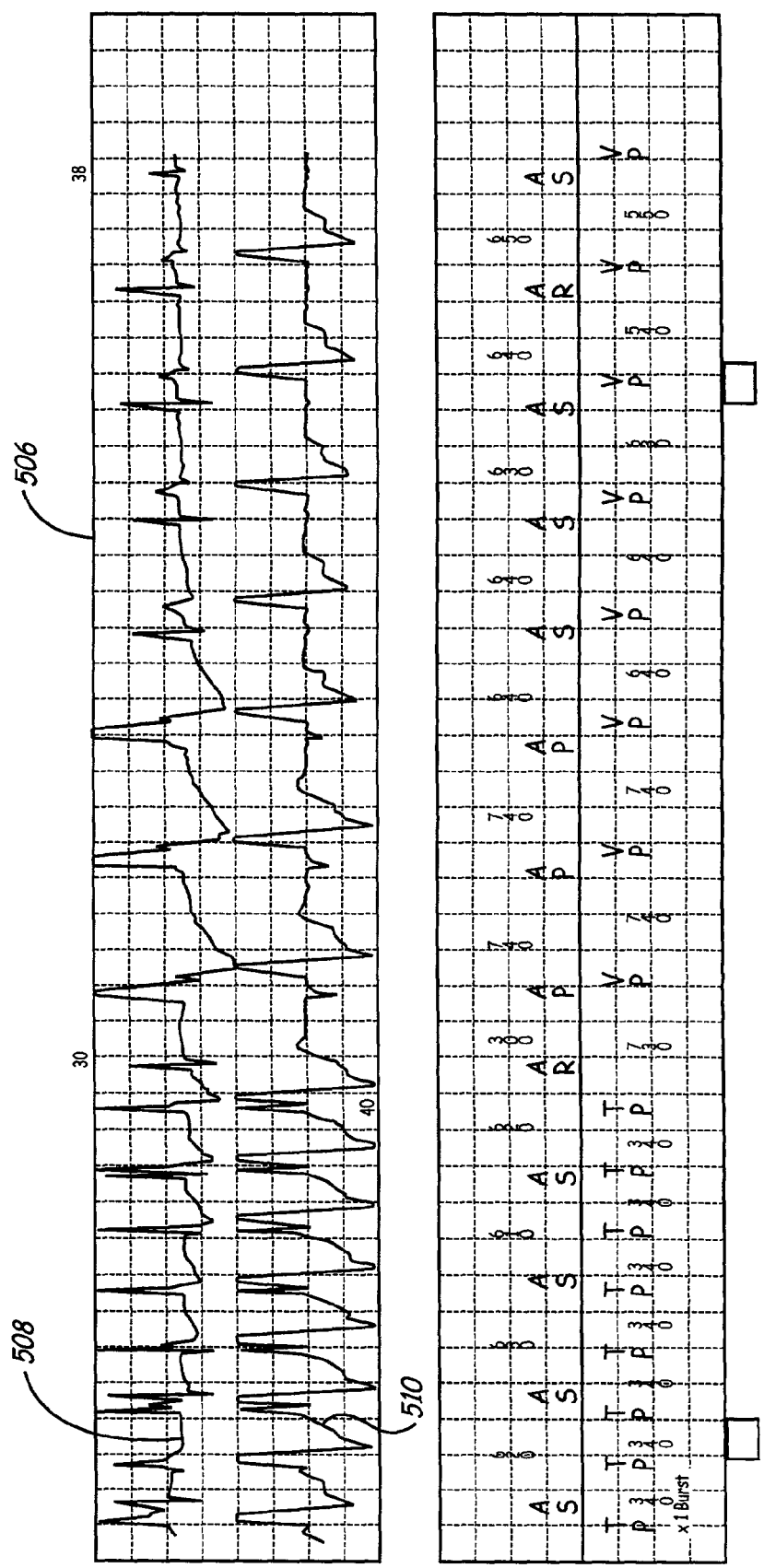

FIG. 3 illustrates a method 400 for preprocessing and analyzing IMD data and outputting visually grouped and annotated versions of that implanted cardiac device data. Prior to describing the details of method 400, the high level operation of embodiment 400 may be described by referring to FIGS. 4-9.

Figure 5A:
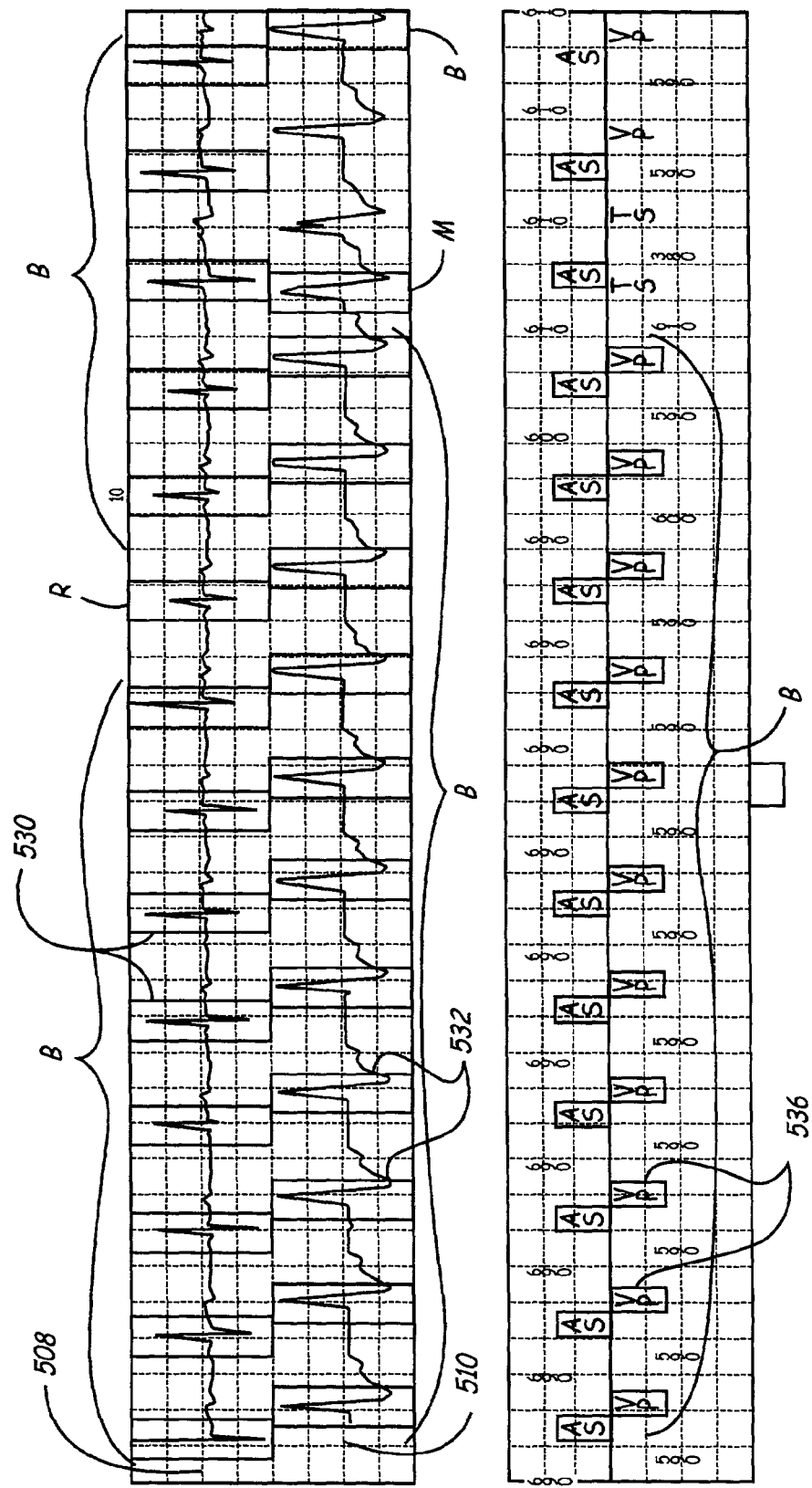
FIG. 5 is a strip chart as in FIG. 4, after the EGM waveforms and intervals have been grouped according to similarity.
Figure 5B:
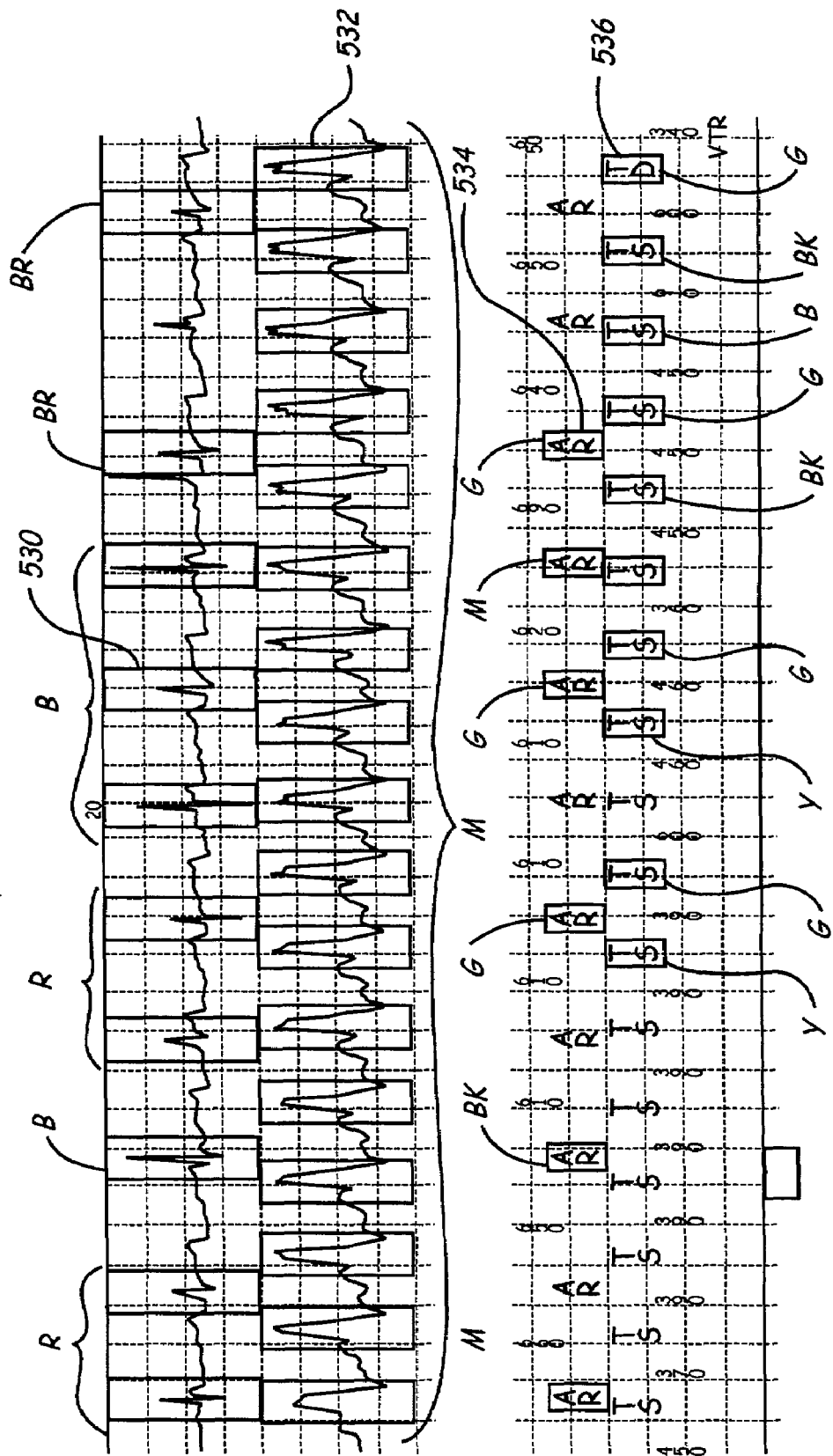
Figure 5C:
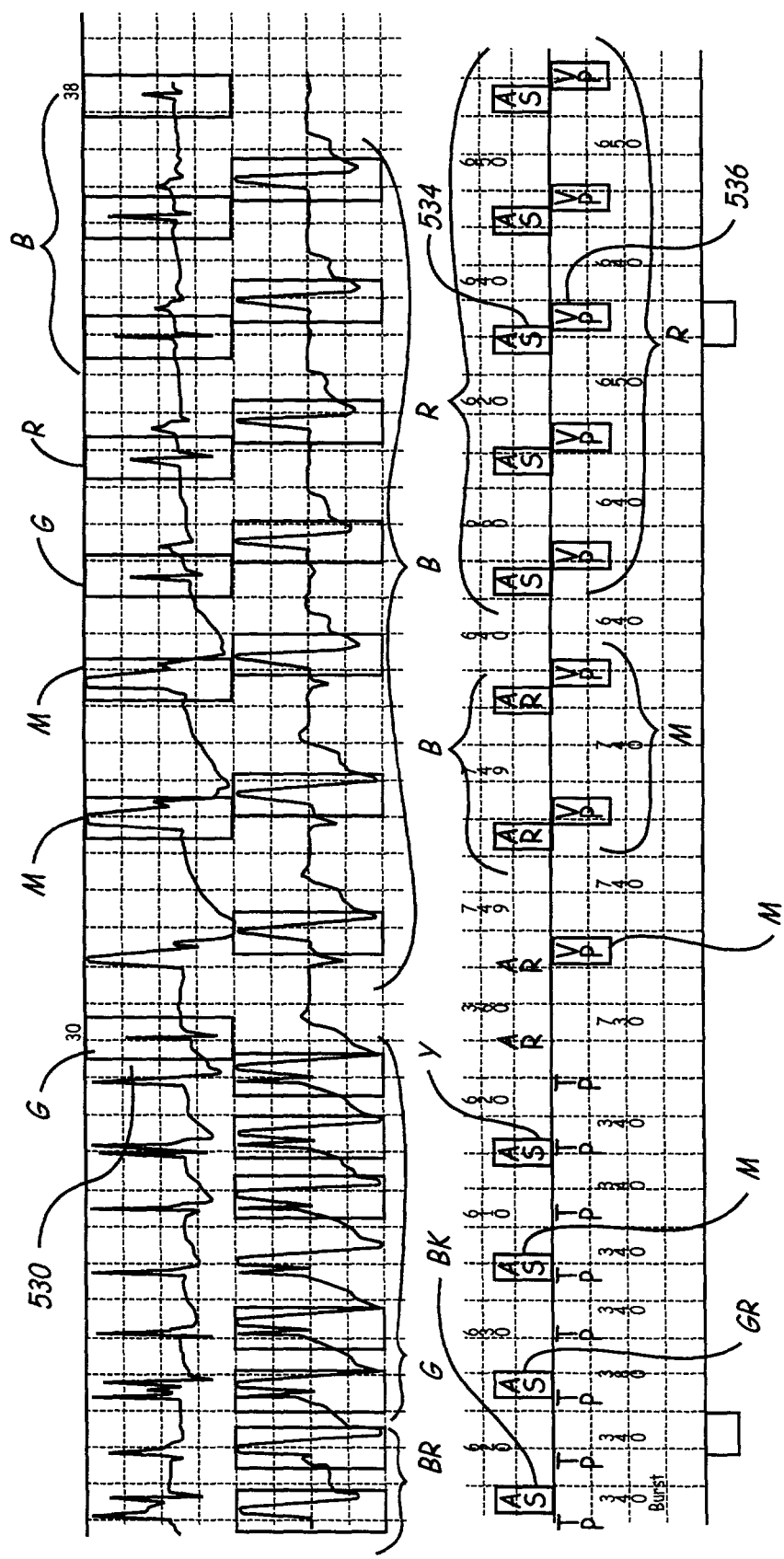
Figure 6A:
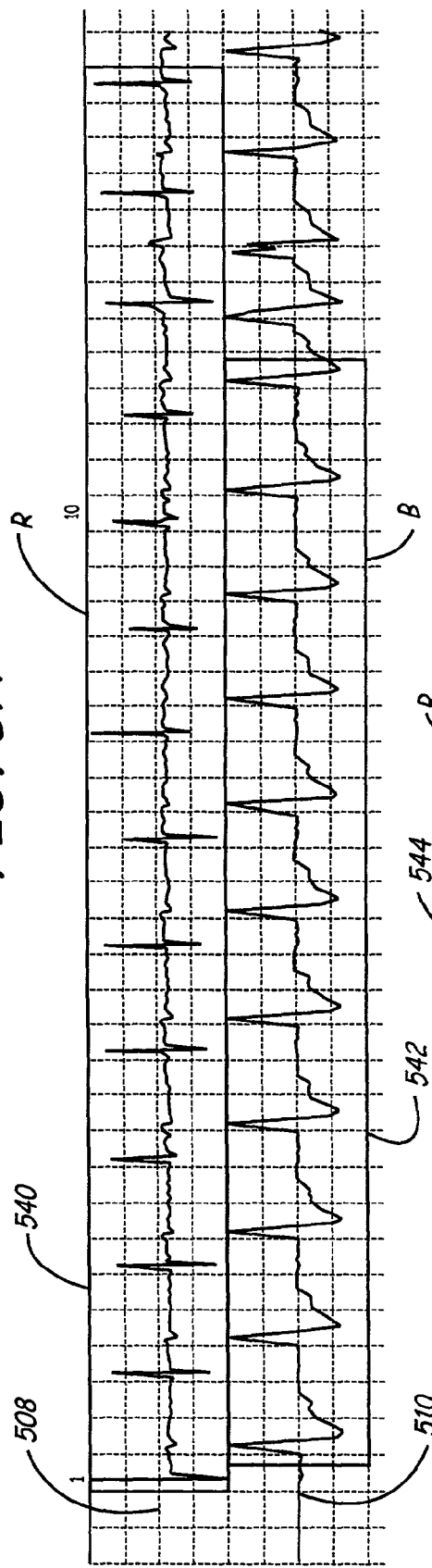
FIG. 6 is a strip chart output as in FIG. 5, after the EGM waveform and interval similarity groups have been further grouped into chronologically contiguous groups.
Figure 6A:
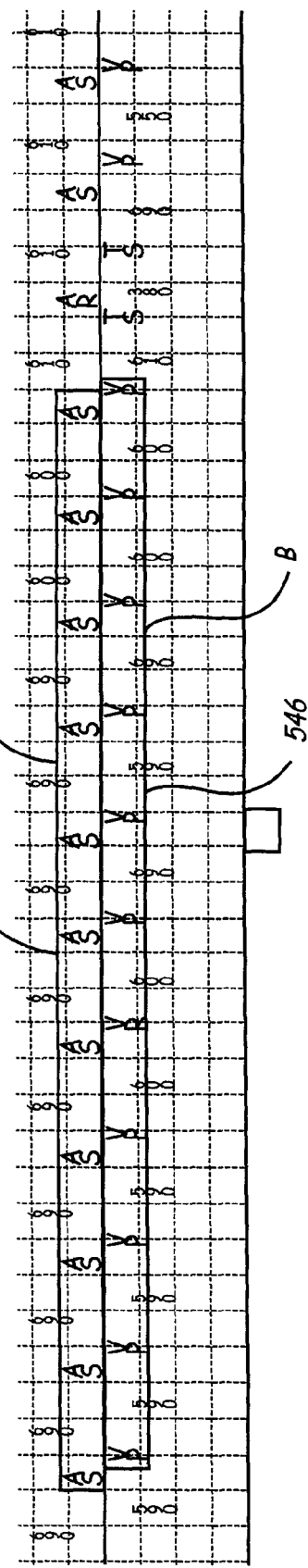
Figure 6B:
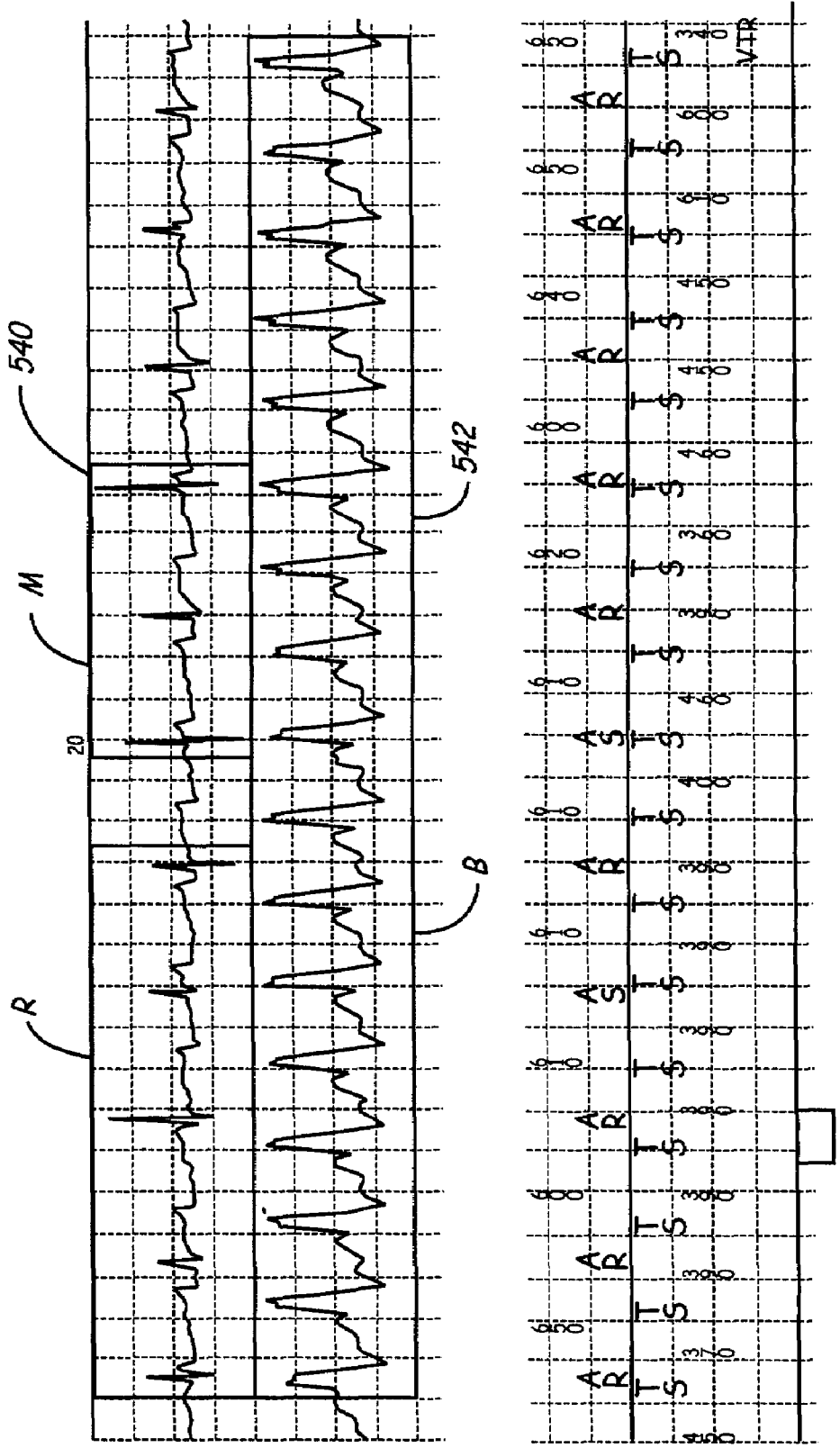
Figure 6C:
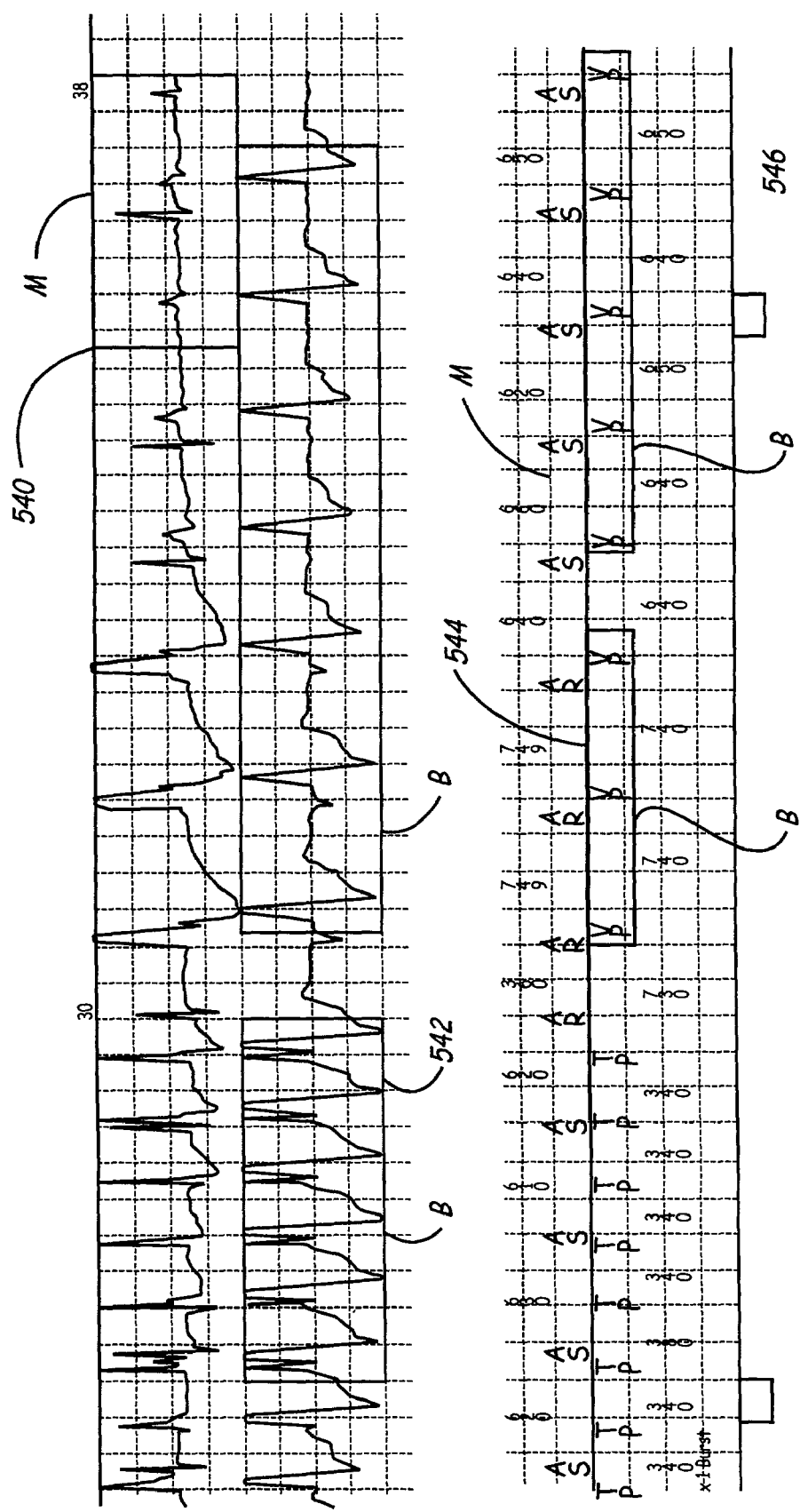
Figure 7A:
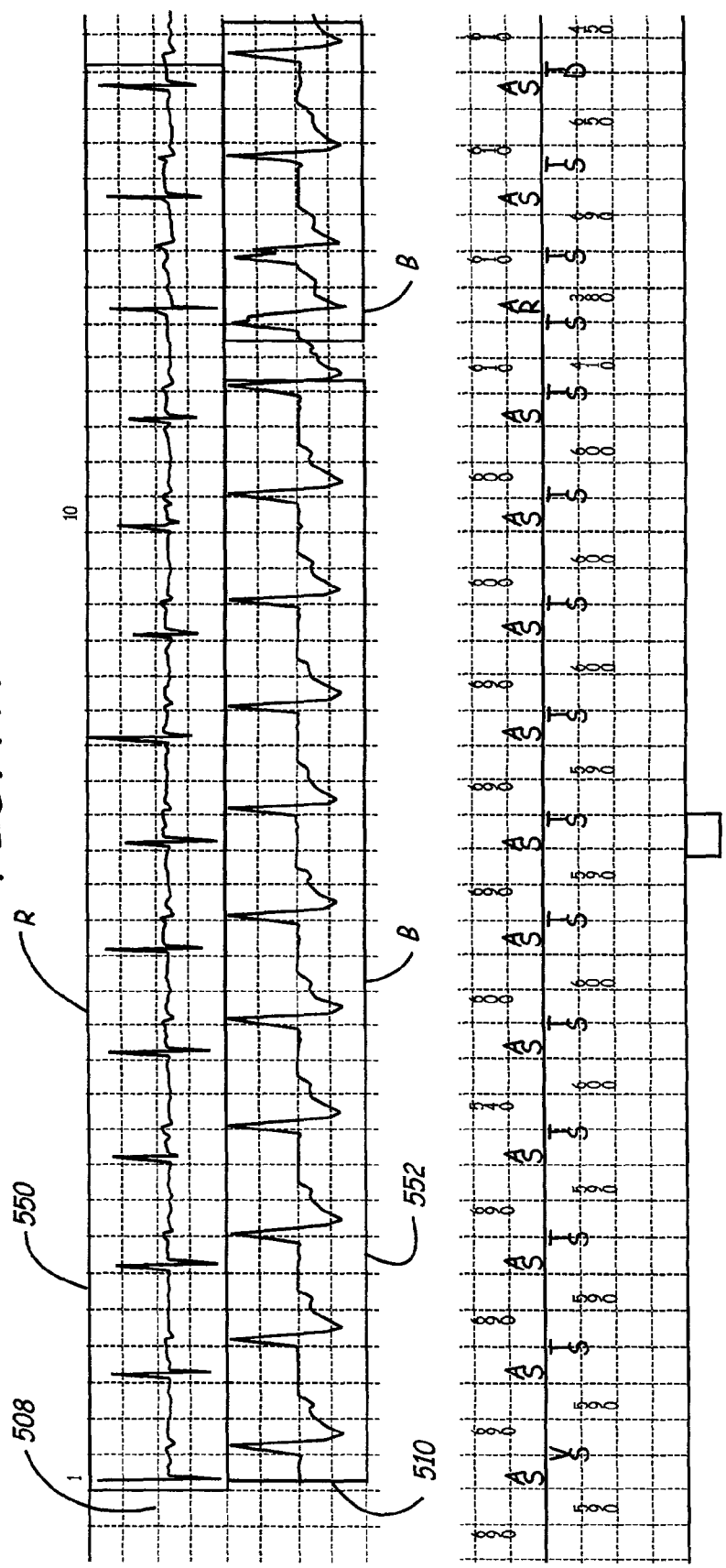
FIG. 7 is a strip chart output as in FIG. 6, after the chronologically contiguous groups of FIG. 6 have been grouped into chronologically co-extensive groups incorporating both EGM and interval data for a single chamber.
Figure 7C:
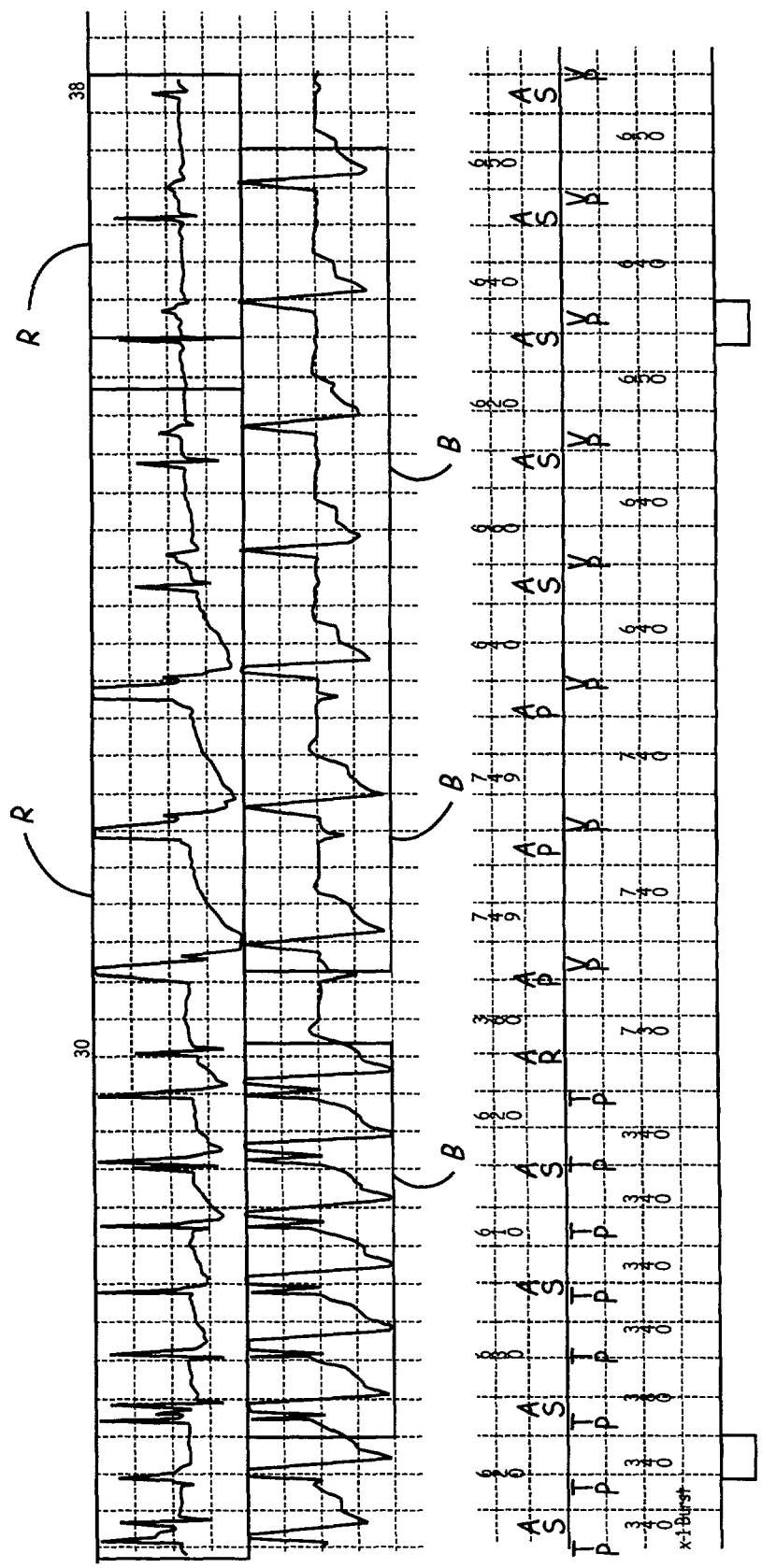
Figure 8A:
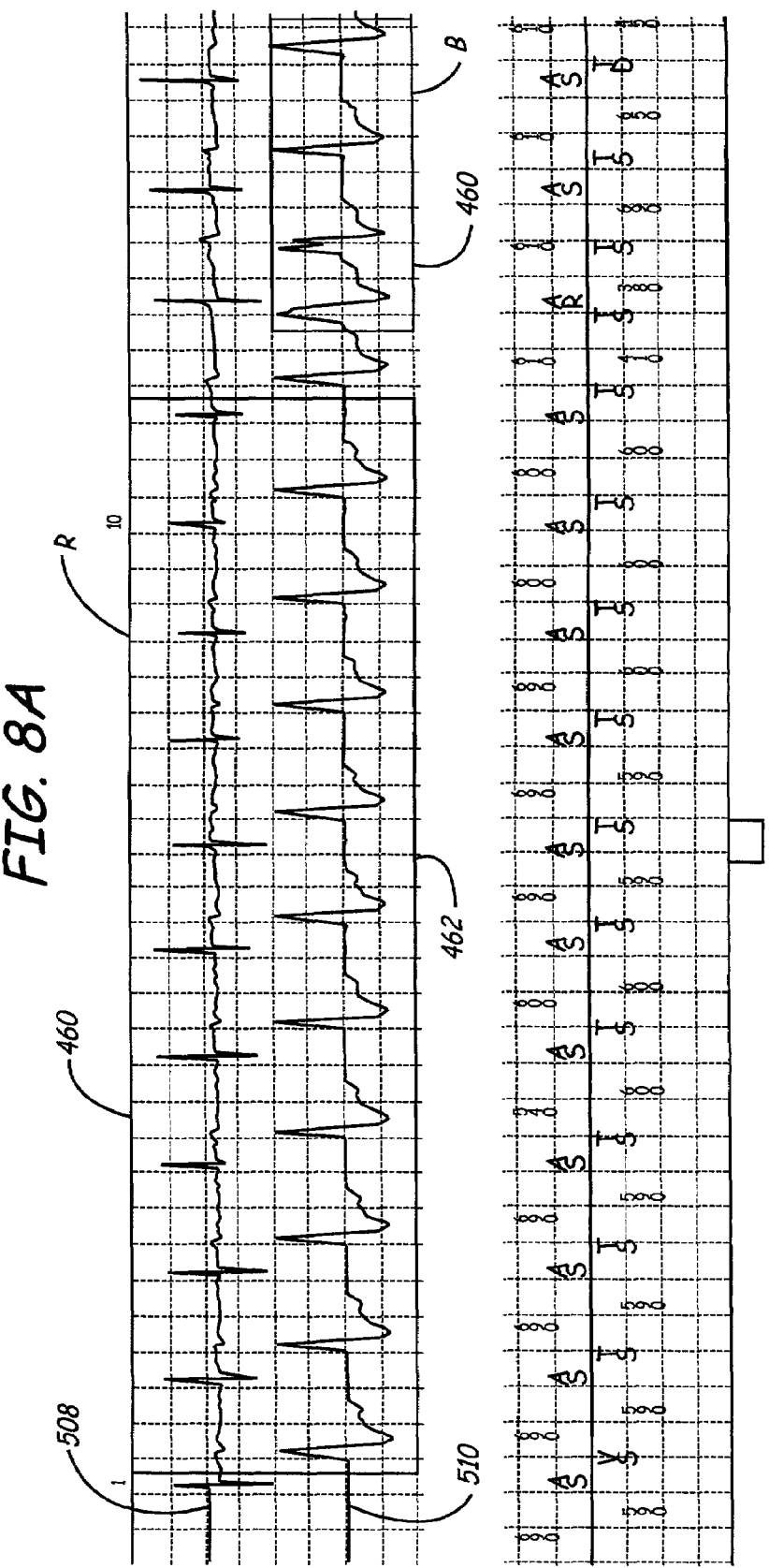
FIG. 8 is a strip chart output as in FIG. 7, having the co-extensive groups of FIG. 7 further grouped into co-extensive groups incorporating both atrial and ventricular groupings, further classified, and analyzed.
Figure 8B:
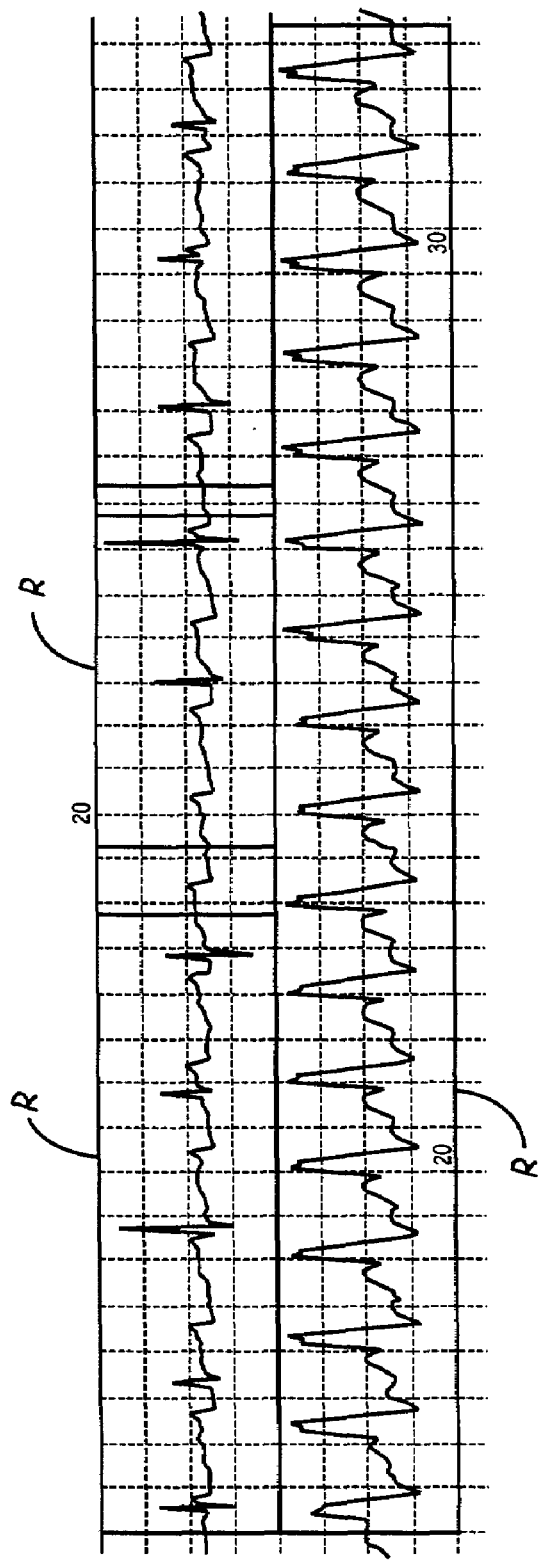
Figure 8B:
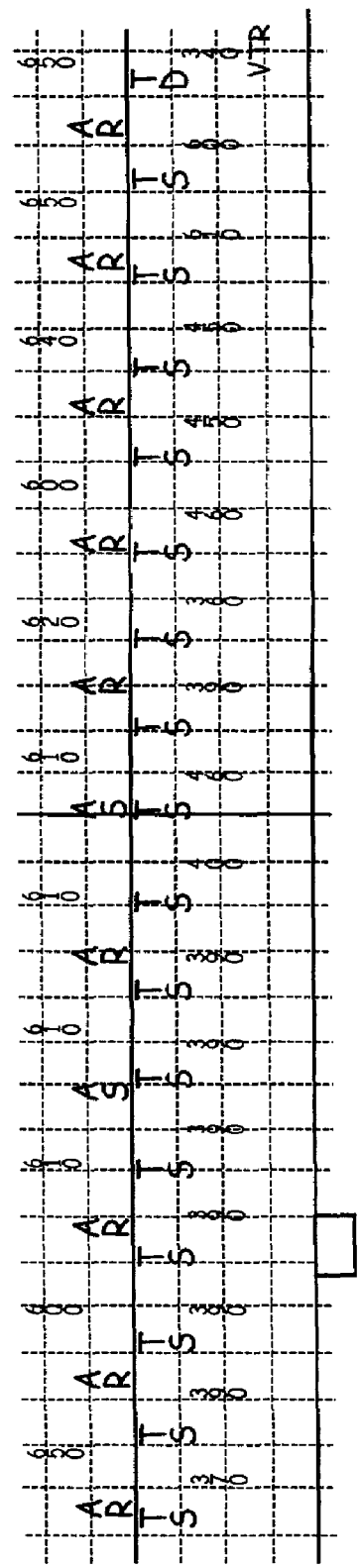
Figure 8C:
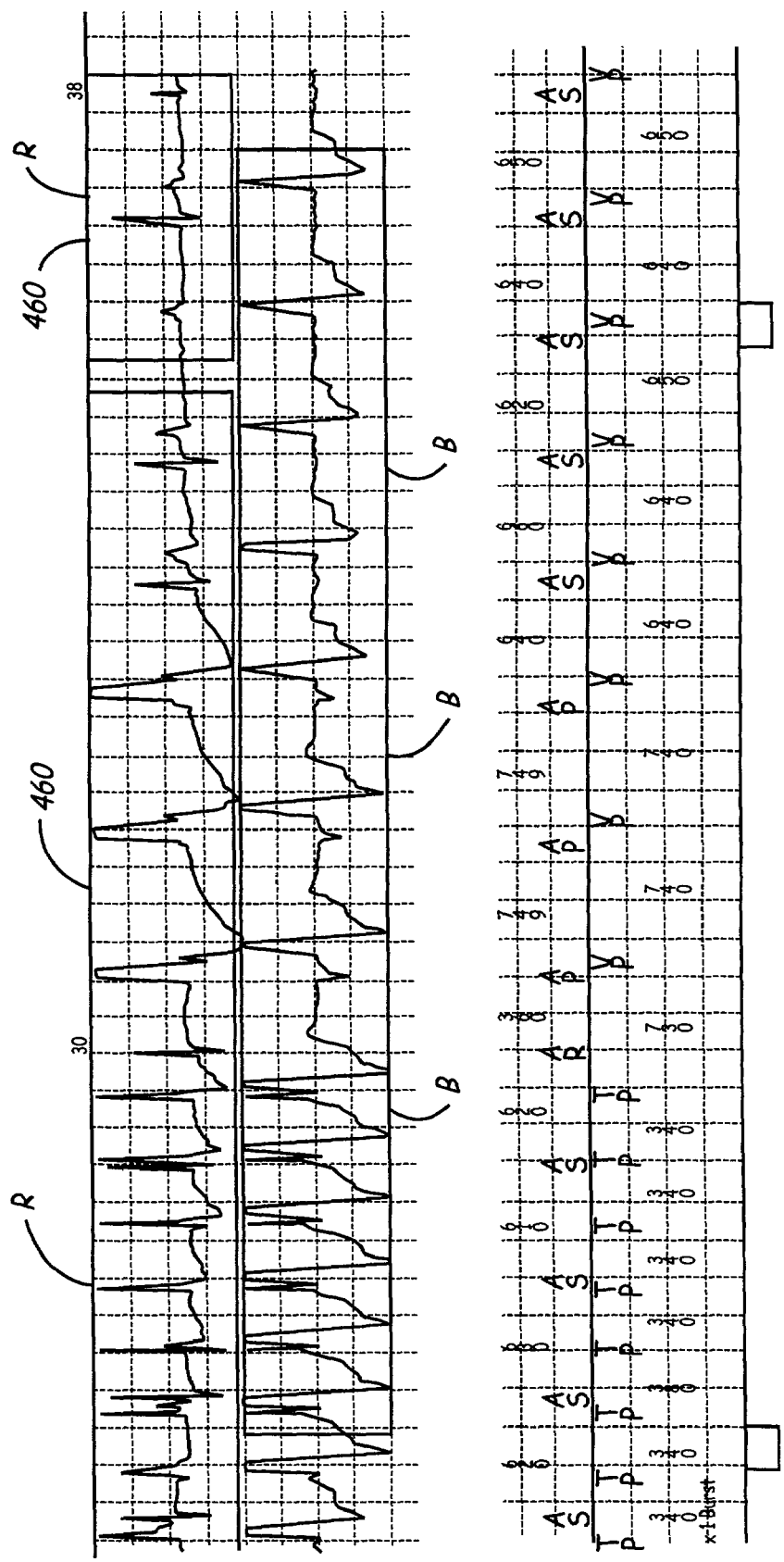
Figure 9C:
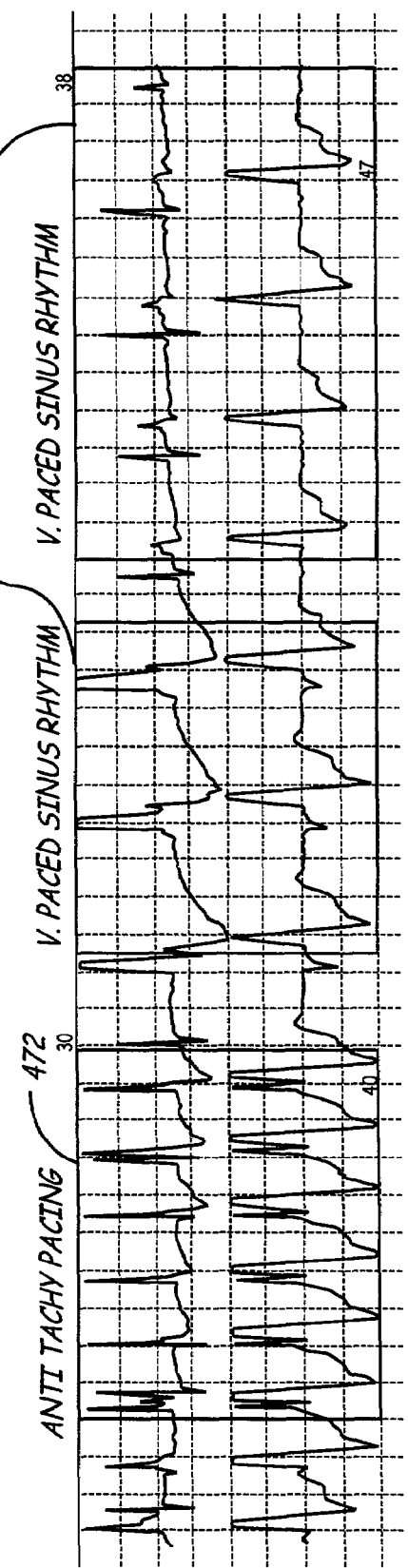
FIG. 9 is a strip chart output as in FIG. 8, having the groups textually annotated as to the pacing regimes found.
Figure 9C:
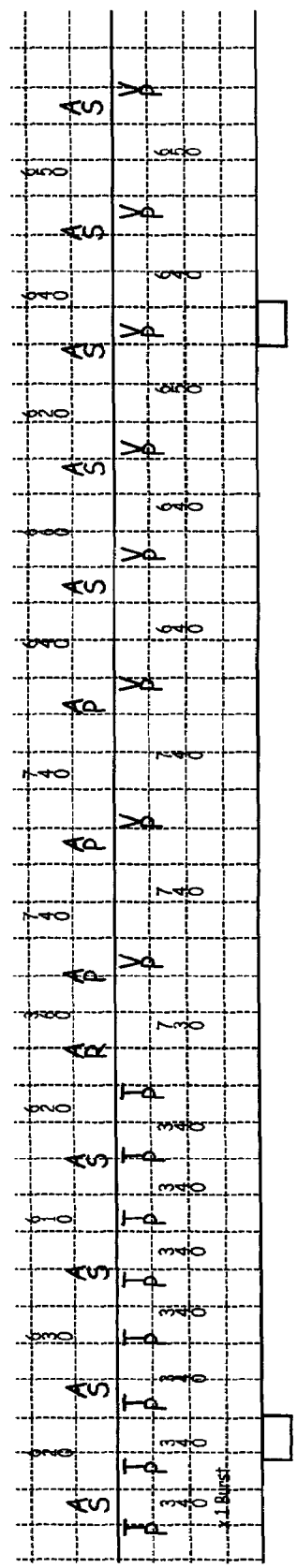

FIG. 4 is a strip chart of IMD data including an atrial EGM waveform plot, a ventricular EGM waveform plot, atrial interval data, atrial marker data, ventricular interval data, and ventricular marker data. FIG. 5 includes the IMD data of FIG. 4, with the data extracted into cardiac cycle segments and grouped into similarity groups, indicated by annotated boxes. FIG. 6 includes the data of FIG. 5, further having similar and chronologically contiguous cardiac cycle further grouped into second level chronologically contiguous beat groups. FIG. 7 includes the data of FIG. 6, having the chronologically contiguous groupings of FIG. 6 further grouped into third level groups which group together chronologically contemporaneous or coextensive arterial EGM data and interval data as well as chronologically contiguous or coextensive ventricular EGM data and interval data. FIG. 8 includes the data of FIG. 7, having the third level groupings further grouped into fourth level groupings encompassing chronologically contemporaneous or coextensive arterial EGM, arterial interval, ventricular EGM, and ventricular interval data. The fourth level groupings of FIG. 8 have further been classified, including classes of waveforms and timings previously established. FIG. 9 includes the IMD data of FIG. 8, having the fourth level classified groups of FIG. 8 further annotated based on the classification and analysis. Embodiment 400 thus proceeds from rather raw implanted cardiac device data as illustrated in FIG. 4 to the analyzed data of FIG. 9 being grouped into five chronological regions.

FIG. 3 illustrates embodiment 400 as beginning with a save-to-disk file retrieval step 402. Steps 402, and 404, are well known to those skilled in the art. Step 402 represents any data retrieval step for retrieving IMD data. The data can originate from IMDs such as pacemakers, and implantable cardioverter defibrillators. In some methods, the IMD data will be retrieved directly from the implanted cardiac device, while in other methods, the data will be retrieved from non-volatile storage long after the data has initially been retrieved through a telemetry link between the implanted cardiac device and a suitable telemetry unit coupled to write to the non-volatile storage. The data retrieval step 402 thus represents any step for retrieving data from non-volatile storage or a data stream of an IMD.

In step 404, a translation utility is used to translate the data retrieved in step 402. The data retrieved in step 402 may often be a purely binary file, requiring translation for further understanding. Translation step 404 can convert the binary file into a text file format from which specific data can more easily be extracted.

In step 406, a translation utility output parser operates on the output of step 404 to extract data for a specific episode or episodes. An episode is the occurrence of a therapy or diagnostic event that may be of particular interest. Some episodes consist of a series of beats in which a device detects and/or treats arrhythmia. The time period may be of interest because of required tachycardia pacing, cardioversion, or required defibrillation. Given a particular episode, the atrial and ventricular EGM can be extracted along with the interval and marker data. The output of step 406 can thus be a time period including numerous cardiac cycles together with associated sensed waveform, interval, and marker data. As is well known to those skilled in the art, the interval data includes the intervals deduced or inferred by the implanted cardiac device. The atrial intervals may be A-A intervals while the ventricular intervals may be V-V intervals. Cross-chamber intervals may also be included, the A-V interval indicating duration from the atrial depolarization to the ventricular depolarization and V-A interval indicating the duration from the ventricular depolarization to the atrial depolarization. The markers are also well known to those skilled in the art and include records stored in IMDs indicating the types of signals collected or therapy delivered to treat a cardiac condition. Examples of atrial markers include AS (atrial sense), AR (atrial refractory sense), and AP (atrial pace). Examples of ventricular markers include VP (ventricular pace), VS (ventricular sense), TD (tachycardia detect), TS (tachycardia sense), and TP (tachycardia pace). Markers are further discussed in U.S. Pat. No. 5,383,909, herein incorporated by reference.

In step 408A, atrial EGM waveforms are clustered, in step 408B, the atrial intervals are clustered, in step 408C, the ventricular EGM waveforms are clustered, and in step 408D, the ventricular intervals are clustered. Similar to FIG. 3 and method 400, the reference number suffix A will be used to refer to atrial EGM data, the suffix B will refer to atrial interval data, the suffix C will be used to refer to ventricular EGM data, and the suffix D will be used to refer to ventricular interval data.

In step 408A, the atrial EGM waveform data may be extracted from the region of each cardiac cycle to form a heartbeat EGM segment associated with each heartbeat. In some embodiments, less than half the total EGM data may be extracted into the cardiac cycle segments at slow heartbeats. In other embodiments, the entire set of EGM data may be extracted, with the cardiac cycle segment data being extracted mainly to divide each heartbeat from the next. While the term "extracted" may be used, the EGM data may of course be left in place and referenced indirectly by the subsequent algorithm steps. The total EGM data may thus be divided into heartbeat segments about each heartbeat, which may still be referred to as the extraction step.

In one extraction or dividing step, the EGM cardiac cycle segments are synchronized with respect to time, such that the predominant peak of each segment is in the same location within each segment. The atrial EGM data may thus be consistently extracted relative to the P-wave while the ventricular EGM data may be consistently extracted with respect to the R-wave. In one method, 15 EGM samples are extracted from about the P-wave to populate the cardiac cycle segment data for the atrial data, while 20 EGM samples are extracted from about the R-wave to populate the cardiac cycle segment data for the ventricular data. In a preferred embodiment of the present invention, the extracted EGM data is used to populate a vector. A vector may be thought of as a one dimensional array but of course may be a multi-dimension array, with one dimension for each cardiac cycle segment. A 15 sample atrial window may thus populate a vector or one-dimensional array having 15 elements while the 20 sample ventricular window may be used to populate a vector or one-dimensional array having 20 elements. In another embodiment, between about 40 and 50 elements from about the QRS complex are used to populate each vector. The time displacement between elements may be inferred from a position within the vector. The relative sizes of the heartbeat segments extracted into the vectors may be visualized with respect to the boxes superimposed over the EGM plots of FIG. 5. While the entire EGM data set may be used, only the data centered about the heartbeat is of primary interest and the extraction step can reduce computation.

With continued reference to FIG. 3 and step 408A, the EGM cardiac cycle segments may be grouped together based on waveform identity. This grouping based on waveform identity or waveform morphology is preferably accomplished by clustering, without an a priori knowledge of the groups into which the heartbeat segments will be grouped. Unlike classification procedures, the number and memberships in the groups are preferably not known a priori. As used herein, the term "clustering" refers to methods used to identify and extract similar groups from a data set based on features of the data set using the proximity of the data set member features.

The distance can be calculated between every vector and every other vector. The vectors can be sorted by closeness to other vectors. In one nearest neighbor method, a first vector is retrieved, and the nearest vector to that first vector saved as the second vector. Then the second vector can be queried to find the vector closest to the second vector, to be saved as the third vector, ignoring vectors that were reviewed earlier. The method can thus proceed through all vectors to produce a sorted array or tree. The output of clustering step 408A can be a single binary tree.

While various clustering algorithms may be used, in a preferred embodiment, nearest neighbor vector clustering is used. The distance between the EGM heartbeat segments may be represented by the distance between the vectors comprising the EGM cardiac cycle segments. In one method, a Euclidean distance is used as the vector distance between the two representative vectors. Other suitable distances may be used, including Mahalanobis distances generally.

The clustering algorithm preferably generates a binary tree where sibling subtrees contain data items that are closer to one another than to any other items in the data set. In the case of two leaf nodes, the two vectors are closer to one another than to any other vectors in the data set. Each node in the tree also contains the actual distance between the closest vectors in right and left subtrees. The tree is ordered such that a parent node always has a closest distance greater than or equal to the closest distance of the right and left subtrees. Clustering in general and nearest neighbor vector clustering are both well documented. In particular, see *Pattern Recognition*, Chapters 11-16, by Theodoridis, et al. (Elsevier Science, 1999), herein incorporated by reference.

In step 410A, a identity threshold can be calculated for the data present in the atrial EGM heartbeat segments. A identity threshold is used to determine whether two waveform vectors are close enough to be considered the same. In some embodiments, the identity threshold is a constant fraction of the average peak-to-peak amplitude for all the waveform segments being compared. The distance between vectors is dependent upon waveform amplitude, so a dynamic threshold based on average maximum amplitude for each beat is more effective than a fixed threshold. This value can be calculated by averaging the peak amplitude for all beats in a given waveform for the episode. The identity threshold is preferably proportional to the average amplitude. For clustering the intervals, a fixed similarity threshold can be used and need not necessarily be calculated. Inspection of FIG. 3 illustrates that the calculate similarity threshold step 410A is receiving input from the translation utility output parser step 406. In some embodiments, step 410 may be considered to obtain output from the translation utility output parser step 406, while in other embodiments, the input may be considered to come from a portion of nearest neighbor vector clustering step 408A. In particular, some extraction or division of the EGM data into the cardiac cycle segments may be performed in step 406 with the output being used by calculate similarity threshold step 410A.

In step 412A, the largest substantially similar subtrees are identified, using the identity threshold output of step 410A and the binary tree output of step 408A. In one method, the sub-tree identification step makes sure that the minimum distances between each leaf node in a subtree and the other leaf nodes in the sub-tree are all less than the identity threshold. The sub-tree identification can also make sure that the maximum distance between all members of a subtree is below a second threshold. If the maximum distance exceeds the second threshold, the members of that sub-tree are not considered to be substantially similar. In other words, in this sub-tree identification step, subtrees are identified that are substantially different from each other so as to constitute both similar waveforms within the subtrees and sufficiently dissimilar waveforms from those of the other subtrees. In one method, the binary tree created in the nearest neighbor vector clustering step is recursively traveled and subtrees are found that meet two criteria. The first criteria is that the closest distance associated with the parent node of the subtree is less than the similarity threshold calculated. The second criteria is that the longest possible distance between any two items in the tree is less than twice the calculated similarity threshold. The output of pruning step 412A is thus a set of one or more subtrees having substantially similar waveform morphologies within each subtree. The particular subtree membership may be stored in or associated with each EGM heartbeat segment for immediate storage, transmission, or visual display. It should be noted that membership within a particular waveform or morphological identity group may be common to waveforms disbursed throughout the episode and/or waveforms chronologically contiguous to one another.

In step 415A, far field R-waves (FFRWs) are found. The subtrees, which have the waveforms and intervals ordered by similarity, can be used in this step also. Step 415A accepts as input the atrial EGM subtrees from step 412A and the atrial interval subtrees from step 412B, to be discussed later.

The FFRW algorithm for one embodiment is further described hereinbelow. The starting point for this algorithm is the sets of atrial beats that have been grouped by morphological similarity. This algorithm only applies to atrial beats. All sets that have greater than 90% of beats meeting FFRW timing criteria are candidates. The FFRW timing criteria for this embodiment require that an atrial beat must precede ventricular beat by less than 50 ms, or must follow the ventricular beat by less than 140 ms.

The following five statistics are preferably gathered on each set. (Statistic 1) The number of beats in the set that are contiguous, as the FFRWs should generally not be contiguous since they occur in addition to real atrial beats. (Statistic 2) The number of beats that have an AA interval within 10% of the next M interval, as the intervals are likely to be different since a FFRW is a false beat interrupting the pattern of the rhythm. (Statistic 3) The number of beats with a morphological difference from the previous beat below a threshold of 0.05*Amplitude, as we would expect a FFRW to have a different morphology from a normal beat. (Statistic 4) The number of beats with a peak-to-peak amplitude greater than 70% of next beat, as it is likely for a FFRW to have a lower amplitude than real beats since it is "far-field". (Statistic 5) The number of beats in the set.

A set of constraints can then be applied to the statistics gathered for each candidate set of beats to declare the set of atrial beats as FFRWs. If any one of these constraints, or rules, is true for a candidate set of beats then all beats in that set are considered to be far-field R-waves.

Rule 1: If Statistic 1=0 and Statistic 4=0 No beats are contiguous and all beats have amplitude of less than 70% of next beat.

Rule 2: If Statistic 1=0 and Statistic 2=0 and Statistic 3<2 No beats are contiguous and no beats have an AA interval within 10% of the next beat and only 1 of the beats is morphologically similar to its previous beat.

Rule 3: Statistic 1=0 and Statistic 3/Statistic 5<0.1 and Statistic>10. No beats are contiguous and less than 10% of the beats are morphologically similar to the previous beat and there are at least 10 beats in the set.

Embodiment 400 of FIG. 3 and sub-tree identification step 412A may be better understood by referring to FIG. 4. FIG. 4 includes generally implantable cardiac device data 500 displayed in a strip chart format as may be output from a programmer, computer, a remote monitor or an equivalent device. IMD data 500 has been divided into three segments for display purposes only. Data 500 thus includes a first portion 502, a second portion 504, and a third portion 506. This same format is repeated in FIGS. 4-9. The top portion of each strip includes generally an atrial EGM plot 508 which includes an electrical potential or millivolt trace over time for the atrium. In this example, atrial trace 508 has been taken from an atrial tip to atrial ring. The amplitude of the atrial pace may be seen by referencing the amplitude marker 512. Atrial trace 508 depicts a predominant P wave peak 514 and substantially flat inter-peak or iso-potential portions 516. Ventricular trace 510 depicts a predominant R wave, separated by inter-peak substantially flat regions 520. Numerous atrial interval values 522 are depicted including atrial markers 524. Similarly, numerous ventricular intervals 526 are shown together with ventricular markers 528.

Referring to FIG. 5, the output of identify subtree step 412A from FIG. 3 may be observed. Atrial trace 508 includes subtree group membership marked for each heartbeat segment or series of segments. The group membership indicates a similar morphology for the EGM waveform. Atrial beat segments 530 (and also the later discussed ventricular trace and atrial and ventricular intervals) have been denoted as belonging to groups "B", "R", "BR", "G", "M", "Y", and "BK", denoting the colors blue, red, brown, green, magenta, yellow and black present on the original colored output, respectively. FIG. 5 illustrates that there are several atrial cardiac cycle segments belonging to group B, followed by a single R group member followed by several more B group members, etc. It should be noted that in this representation the morphologically similar cardiac cycle segments were grouped according to waveform or morphology similarities, not in chronological relation to each other.

With continued reference to FIG. 3, method 400 may be further discussed, beginning with step 414A. In step 414A, chronologically contiguous and similar beats are found. In one method, each subtree found with beats of similar morphology is recursively traversed to find ranges of contiguous beats or substantially contiguous beats contained within that tree. Single beat exceptions may be allowed and the exception beats for each range along with the possible diagnosis of the beat (e.g., FFRW, PVC, PAC, and PACED or unknown) are associated with the contiguous range. The term "chronologically contiguous" may be used even though the beats need not be chronologically adjacent, but may be distant from one another by one or more beats, depending on the embodiment. In a preferred embodiment, as previously discussed, the beats may be considered as contiguous even when the contiguous sequence is interrupted by a beat from a different group. The output of the identify subtree step 412A may be considered as a first level grouping of heartbeat segments, and the output of step 414A considered as a second level grouping of beat segments using chronology. The output of step 414A may be visualized with respect to FIG. 6. Chronologically contiguous similar beat segments have been grouped into groups 540 denoted by group membership notations R, B, M, as previously discussed as describing the colors of the original plot.

Further referring to FIG. 3, the processing of the atrial intervals may be discussed, beginning with step 408B. In step 408B, the intervals are clustered into identity groups, in a method somewhat similar to that used in step 408A. In step 408B, the similarity threshold is preferably fixed. Nearest neighbor clustering is the preferred clustering algorithm used in step 408B. The output of step 408B is preferably a single binary tree which is operated on by step 412B which identifies similar subtrees. Step 412B uses a similar method as described with respect to 412A, previously discussed. The output of identify sub-tree step 412 is preferably a series of subtrees, with each subtree containing similar intervals. The output of identify sub-tree step 412B may be visualized by referring again to FIG. 5. The atrial markers 534 of FIG. 5 have been grouped into similarity groups once again denoted arbitrarily by a letter code denoting the color output in one embodiment of the invention, previously described. In one method, the interval similarities are denoted by color coding the markers and/or surrounding the markers with a color coded box, as seen in FIG. 5.

With continued reference to FIG. 3, step 414B accepts the output from step 412B and finds chronologically contiguous similar beats in a manner similar to step 414A previously discussed. The output of step 414B may be visualized by referring again to FIG. 6. In FIG. 6, the chronologically contiguous similar intervals have been grouped into a second level grouping seen at 544 and assigned a group notation once again corresponding to the color of the original output. In the top strip of FIG. 6, the chronologically contiguous and similar atrial intervals have been grouped into group 544.

Before proceeding to step 416A, the steps for processing the ventricular data may be briefly discussed. The ventricular data can be processed similar to the atrial data. Thus, step 408C is similar to step 408A, 408D is similar to step 408B, step 412C is similar to step 412A, step 412D is similar to step 412B, step 414C is similar to step 414A, step 414D is similar to step 414B, and step 410C is similar to step 410A. Referring again to FIG. 5, ventricular EGM heartbeat segments 532 have been grouped into waveform or morphological similarity groups denoted by the letter or color codes previously described. Similarly, the ventricular intervals 536 have been grouped into similarity groups denoted by the letter or the color codes previously described. FIG. 6 shows the ventricular EGM waveforms further grouped into the chronologically contiguous groups 542 and assigned the letter or color codes previously discussed. Similarly, the ventricular intervals have been further grouped into the chronologically contiguous groups 546, in a manner previously discussed with respect to the atrial interval chronologically contiguous groups.

With continued reference to FIG. 3, step 416A may be discussed. In step 416A, consistent (chronologically co-extensive or contemporaneous) atrial segments are found. In this step, each channel is partitioned into segments of similar pattern. The segments may consist of similar morphology and interval pattern, just similar morphology pattern, just similar interval pattern, or no pattern. Segments that consist of both similar morphology and interval pattern are found by taking the intersection of overlapping contiguous ranges of morphology pattern and interval pattern. If the EGM segment is greater than 10% longer than the interval segment, then the interval pattern similarity is ignored in one embodiment. When a segment is created consisting of both similar EGM morphology pattern and interval pattern, then the exception list of those two ranges are merged. The exception list is simply a list of beats in the contiguous segment with dissimilar morphology or interval pattern. Segments of the episode that are not covered by either an interval segment or an EGM segment can also be identified as a pattern-less segment. Step 416C operates in a manner similar to step 416A, with step 416C operating on ventricular data. Step 416A thus accepts the second level or chronological groupings from steps 414A and 414B, and, where appropriate, further groups them into a third level group. This third level group thus can encompass both the EGM waveform chronological grouping and the interval chronological grouping for a single chamber.

The output of steps 416A and 416C may be visualized by referencing FIG. 7. In FIG. 7, the third level grouping output from steps 416A and 416C is again denoted by boxes drawn about the EGM waveforms at 550 and 552 and marked with the letter or color code.

With continued reference to FIG. 3, step 424 may be discussed. In step 424, consistent (chronologically co-extensive or contemporaneous) episode segments are found. In this step, the episode is divided into segments of common pattern using both chambers and using both EGM and interval patterns. In a preferred embodiment, the intersection of segments being combined across chambers must be at least 60% of the size of the original segments. The segments with the greatest number of common patterns are preferably found first. In a preferred embodiment, EGM pattern segments are favored over interval pattern segments. Segments with no pattern can also be identified.

In step 418, interval statistics can be computed. For a given range of beats in a chamber, the interval average and standard deviation can be computed. Also, over the same range, the average difference between the EGM vectors and the standard deviation of that difference can also be computed.

In step 420, the conduction pattern can be classified. In this classification, all atrial interval trees with beats in the range of the specified segments can be found. Then it may be determined whether all beats from each tree are equally distributed throughout the range. If so, this indicates a repetitive interval pattern characteristic of non-one-to-one conduction. The ratio of atrial beats to ventricular beats indicates the actual conduction pattern. For retrograde conduction, the same procedure can be used, but driven from the ventricular channel rather than the atrial channel.

In step 422, the conduction direction can be classified. The AV and the VA interval standard deviation through the specified range can be used to determine whether the conduction is antegrade or retrograde. If the AV interval is more stable within a specified range, antegrade conduction is indicated. If the VA interval is more stable within a specified range, retrograde conduction is indicated.

In step 426, the results of steps 418, 420, 422 and 424 may be used as input. In step 426, the conduction pattern, conduction direction, rate, and EGM and interval patterns found in this segment are used to provide a classification for the atrium and ventricle in the given segment of the episode. Classification methods in general are well known. See U.S. Pat. No. 6,217,525 and Pattern Classification and Scene Analysis, by R. Duda and P. Hart, (pub. John Wiley & Sons), both herein incorporated by reference.

The output of step 416 may be visualized by referring to FIG. 8. In FIG. 8, the fourth level groupings from step 416 are illustrated. A result for one such analysis may be discussed for group 462 of FIG. 8. In an actual embodiment of the invention, grouping 462 was classified as having an episode segment from ventricular beat 1 to atrial beat 11. This extended from 710 milliseconds to 6520 milliseconds, having a duration of 5810 milliseconds. A segment pattern was found in the ventricular EGM, the atrial EGM, the ventricular interval, and the atrial interval. For the atrium, there were 10 beats, zero paced, 10 sensed, zero therapy, and zero FFRW. For the ventricle, there were 10 beats, 10 paced, zero sensed, and zero therapy. For the atrium, the average interval was 593 milliseconds with a standard deviation of five milliseconds. The ventricle had an average of 592, with a standard deviation of four milliseconds. The VA interval averaged 473 with a standard deviation of five milliseconds. The AV interval averaged 120 with a standard deviation of zero. This grouping was analyzed and classified as having a sinus atrial rhythm, conduction of one-to-one antegrade, and a VPACE ventricular rhythm. The discussion of group 462 is for purposes of illustration. Similar types of analysis and classification can be provided for the other groups.

Referring again to FIG. 3, annotation step 428 may be discussed. In step 428, a final classification of the segment or group is determined based on the atrial and ventricular classifications. A text string can be generated to annotate that segment of the episode. The output of step 428 may be visualized with respect to FIG. 9.

In FIG. 9, the groupings of FIG. 8 have been further analyzed as previously discussed. Group 470 can be annotated to indicate a VPACED sinus rhythm. Group 472 can be annotated to indicate ventricular tachycardia. Group 474 can be annotated to indicate antitachycardia pacing. Group 476 can be annotated to indicate ventricular paced sinus rhythm. Finally, group 478 can be annotated to indicated ventricular paced sinus rhythm.

Figure 10A:
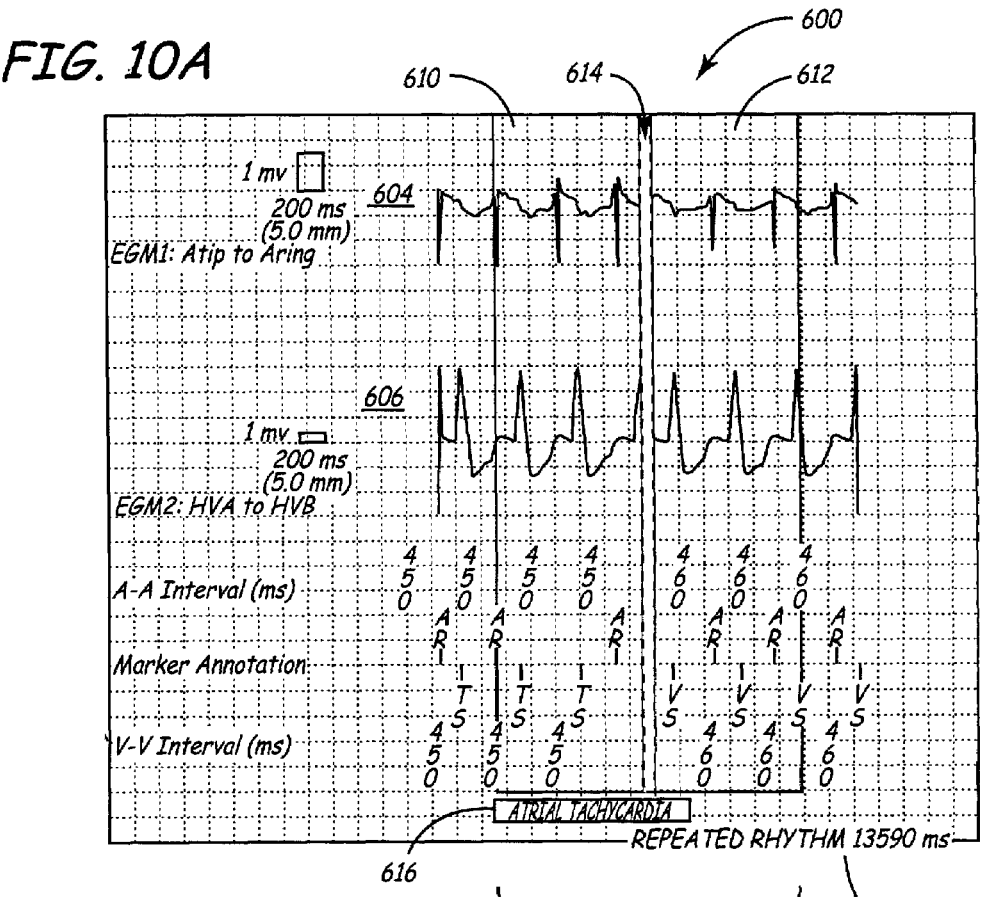
FIG. 10A is a strip chart output portion utilizing a compressed waveform display.

FIG. 10A illustrates another aspect of the invention including waveform compression. A strip chart display 600, which was taken from a programmer display, includes a first sensor channel 604 and a second sensor channel 606. In this example, first channel 604 includes an atrial EGM waveform and second channel 606 includes a ventricular EGM waveform. A compressed cardiac waveform region 602 includes a first end waveform region 610 and a second end waveform region 612, separated by a break or omitted region 614. Compressed region 602 contains a region having chronologically co-extensive, chronologically contemporaneous and morphologically similar atrial waveforms and chronologically contemporaneous and morphologically similar ventricular waveforms. The length of region 602 has been compressed by displaying the first waveforms at 610, the last waveforms at 612, with a break for the middle, similar, omitted waveforms, at 614. The length of the repeating waveform region at 614 has been indicated at 618, to be 13590 ms in length. In some embodiments, the length of the repeating, omitted region, is indicated in units of time and/or beats. The classification of the repeating waveform is indicated at 616 to be Atrial Tachycardia.

Figure 10B:
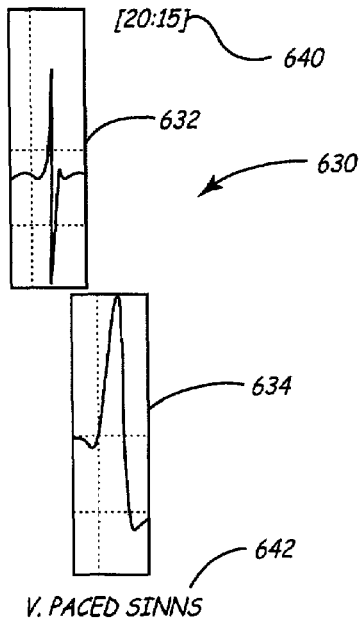
FIG. 10B is a strip chart output representation of a waveform exemplar.

FIG. 10B illustrates another compression method according to the present invention. An example of a waveform grouping 630, termed an "exemplar", has been displayed, rather than displaying a long run of morphologically, repeating waveforms. Exemplar 630 includes a first sensor waveform exemplar 632, of an atrial EGM, and a second sensor waveform exemplar 634, of a ventricular EGM. Exemplar 630 is a grouped or composite exemplar including both exemplars 632 and 634. A repeat length indicator 640 indicates the length of the repeating group in both seconds and number of beats. A classification indication 642 indicates that the exemplar has been classified as a region of V. Paced Sinus Rhythm. Exemplars can be put to a first use in compression, as in FIG. 10B, to represent a long series of grouped and similar waveforms, by displaying one of the similar waveforms together with an indication of the number of repeats, rather than displaying every one of the similar waveforms.

In a second use of exemplars, a single waveform exemplar can be stored and/or transmitted, along with a repeat indicator, to represent a much longer series of waveforms. The received exemplar can be represented as an exemplar and/or uncompressed into a representation of the original long series of waveforms.

In a third use of exemplars, an exemplar can be selected and presented to a clinician as a representative waveform from an arrhythmia. In a fourth use, an exemplar can be selected from two or more different episodes, and the exemplars compared to determine if the arrhythmia is the same. In this way, two arrhythmias from different times for the same patient can be automatically compared for waveform similarity.

Exemplars can be selected from according to different levels of grouping in different methods. Exemplars can be selected to represent a first level of morphologically similar waveforms, a second level of similar and chronologically contiguous waveforms, a third level requiring multiple sensor or multiple channel chronologically contiguous waveforms, and so forth.

In one embodiment of the invention, the cardiac sensor data is input to a software program previously described where the program implements some or all of the parts of method 400 of FIG. 3. The output of some programs may simply assign and store the various group memberships previously described for the heartbeat segments. This grouping can be later transmitted or displayed. In a preferred embodiment of the invention, the output includes a visual output, preferably in color, and annotated as discussed with respect to FIGS. 4-10.

The detailed descriptions of the preferred embodiments provided herein yield an accurate, efficient and reliable apparatus and methods to analyze, compile, classify and identify cardiac cycle events including therapy, diagnostic events and signal morphologies acquired from an implantable medical device. Numerous variations of the described embodiments are possible for practicing the invention. Therefore, the embodiments described herein should be considered exemplary, rather than limiting, with regard to the following claims.

What is claimed is:

1. A method for analyzing stored cardiac EGM waveform data for a plurality of a first heart chamber cycles, the data including a plurality of waveform cycle segments, the data initially originating from an implanted device, the method comprising:
    grouping the waveform cycle segments into a first set of cycle groups as a function of waveform shape similarity between the waveform cycle segments, wherein each of the first set group members have similar waveform shapes to the other members of the same first set group;
    wherein the grouping includes clustering the waveform cycle segments based on waveform shape similarity;
    wherein the waveform cycle segments are treated as vectors; and
    wherein the clustering clusters includes using the Euclidean distance between the vectors.

2. A method as in claim 1, wherein the clustering includes nearest neighbor clustering.

3. A method as in claim 1, further comprising:
    grouping the waveform cycle segments into a second set of cycle groups, wherein the second set group members are substantially chronologically contiguous to the other second set group members and are members of the same first set group.

4. A method as in claim 3, further comprising processing the first set groups by executing one of a step of marking, storing, displaying, and outputting the group memberships, and combinations thereof.

5. A method for analyzing stored cardiac EGM data from an implantable device, the method comprising:
    retrieving the stored data, wherein the data includes EGM waveform data;

dividing the EGM waveform data into a plurality of cardiac cycle waveform segments, wherein each heartbeat waveform segment is associated with a heartbeat; and grouping the EGM cardiac cycle waveform segments into waveform identity groups as a function of waveform shape similarities between the waveform segments with members of the same waveform identity group having similar waveform shapes to the other waveform identity group members;

wherein the grouping includes calculating a waveform shape distance between the cardiac cycle waveform segments and clustering the cardiac cycle waveform segments as a function of the shape distance between the heartbeat waveform segments;

wherein each cardiac cycle waveform segment is represented as a vector and the shape distance is a distance between the vectors; and wherein the vector distance is a Euclidean distance.

6. A method as in claim 5, further comprising marking the EGM heartbeat waveform segments with an indicia of identity group membership and storing the marked EGM identity waveform segments in nonvolatile storage.

7. A method as in claim 5, further comprising the step of visually displaying the EGM heartbeat waveform segments together with a visual indicia of the waveform identity group membership for each EGM heartbeat waveform segment.

8. A method as in claim 5, further comprising collecting temporally adjacent heartbeat waveform segments having the same heartbeat waveform identity group membership into chronologically contiguous similar cardiac cycle waveform segments.

9. A method as in claim 8, wherein the temporally adjacent cardiac cycle waveform segments are located at a distance at no more than n cardiac cycles from each other, wherein n is selected from a group consisting of 1, 2, and 3 cardiac cycles, wherein n=0 indicates perfect adjacency.

10. A method as in claim 8, further comprising marking the collections with indicia of collection membership and storing the marked collections to nonvolatile storage.

11. A method as in claim 8, further comprising visually displaying the collections with a visual indication of cardiac cycle waveform segment collection membership.

12. In a computer, having a data storage device, a display device, and a processor for executing a program, a method for preprocessing stored cardiac data originating from an implantable device, the method comprising:

retrieving the stored data from the data storage device, wherein the data includes EGM waveform segment data for a plurality of beats for a first heart chamber;

clustering the EGM waveform segments into morphological similarity groups having similar morphology with other members of the same group; and organizing morphologically similar and substantially chronologically contiguous cardiac cycle segments into collections of similar and substantially chronologically contiguous cycles wherein the retrieved EGM waveform data is stored as a vector of wave amplitudes for each cardiac cycle segment;

wherein the clustering includes clustering the EGM waveform vectors using nearest neighbor vector clustering; and wherein the clustering utilizes Euclidian distance between the EGM waveform vectors to cluster the EGM waveforms.

* * * * *

UNITED STATES PATENT AND TRADEMARK OFFICE
CERTIFICATE OF CORRECTION

PATENT NO. : 7,263,399 B2  Page 1 of 1
APPLICATION NO. : 10/135910
DATED : August 28, 2007
INVENTOR(S) : Dan B. Carlson It is certified that error appears in the above-identified patent and that said Letters Patent is hereby corrected as shown below:

Col. 20, line 30, please delete "utilizes Euclid ian" and replace with
--utilizes Euclidian--.

Signed and Sealed this

Twenty-fifth Day of March, 2008

JON W. DUDAS
*Director of the United States Patent and Trademark Office*